United States Patent [19]
Armitage et al.

[11] Patent Number: 5,464,781
[45] Date of Patent: Nov. 7, 1995

[54] AMINO NAPHTHYRIDINE COMPOUNDS AS ANTI-RHOUMATIC AGENTS

[75] Inventors: Bernard J. Armitage; John G. Bowen; Malcolm J. Crossley; Ian M. Hunneyball; Bruce W. Leslie; Thomas K. Miller; Michael Spowage, all of Nottinghamshire, England

[73] Assignee: The Boots Company PLC, Notts, England

[21] Appl. No.: 244,369

[22] PCT Filed: Oct. 12, 1992

[86] PCT No.: PCT/EP92/02901

§ 371 Date: Jun. 3, 1994

§ 102(e) Date: Jun. 3, 1994

[87] PCT Pub. No.: WO93/13097

PCT Pub. Date: Jul. 8, 1993

[30] Foreign Application Priority Data

Dec. 23, 1991 [GB] United Kingdom .............. 9127252

[51] Int. Cl.$^6$ .................. A61K 31/435; C07D 47/04
[52] U.S. Cl. .................. 514/300; 544/127; 546/122
[58] Field of Search .................. 546/122, 159; 514/300, 313

[56] References Cited

U.S. PATENT DOCUMENTS

| | | | |
|---|---|---|---|
| 4,801,592 | 1/1989 | Graf | 514/300 |
| 5,143,920 | 9/1992 | Ite | 514/313 |

FOREIGN PATENT DOCUMENTS

| | | |
|---|---|---|
| 0181568 | 5/1986 | European Pat. Off. . |
| 0302303 | 2/1989 | European Pat. Off. . |
| 0361177 | 4/1990 | European Pat. Off. . |
| 0410762 | 1/1991 | European Pat. Off. . |
| 0452873 | 10/1991 | European Pat. Off. . |
| 7229519 | 8/1972 | Japan . |
| 63-068568 | 3/1988 | Japan . |
| 84/00489 | 2/1984 | WIPO . |
| 86/06718 | 11/1986 | WIPO . |
| 90/14338 | 11/1990 | WIPO . |

OTHER PUBLICATIONS

Weinblatt M. E. Maier Al. Disease–Modifying agents and experimental treatments of rhematoid arthritis Clin. Orthop (1991 Apr.) 265 103–15.
Sofia et al., Comparative Effects of Anti–Arthritic and Other Pharmacological Agents in the 18–hour Arthritis and Carrageenan Edema Tests in Rats. Pharm. Res. Comm. 11, No. 2, 179–193 (1979).
Barlin et al., Potential Antimalarials. 1. 1,8–Naphthyridines. Aust. J. Chem. 37, 1065–1173 (1984).
Kuroda et al., A Novel Synthesis and Potent Antiinflammatory Activity of 4–Hydroxy–2(1H)–oxo–1–phenyl–1, 8–naphthyridine–3–carboxamides. J. Med. Chem. 35, 1130–1136 (1992).
Heber et al., Synthesis of 2– and 4–alkylamino–1, 8–naphthyridine Derivatives as Potential Positive Inotropic Agents. Arch. Pharm. 324, No. 9, p600 (1991).
Crossley et al., Studies on the Effects of Pharmacological Agents on Antigen–Induced Arthritis in BALB/c Mice. Drugs Exptl. Clin. Res. XIII (5) 273–277 (1987).
Hunneyball et al., Pharmacological Studies of Antigen–Induced Arthritis in BALB/c Mice I. Characterization of the Arthritis and the Effects of Steroidal and Non–Steroidal Anti–Inflammatory Agents. Agents and Actions 18, 3/4 384–393 (1986).
Hunneyball et al., Pharmacological Studies of Antigen–Induced Arthritis in BALB/c Mice II. The effects of second–line antirheumatic drugs and cytotoxic agents on the histopathological changes. Agents and Actions 18, 3/4 394–400 (1986).

*Primary Examiner*—C. Warren Ivy
*Assistant Examiner*—Evelyn Huang
*Attorney, Agent, or Firm*—Nikaido, Marmelstein, Murray & Oram

[57] ABSTRACT

This invention relates to compounds of formula I and pharmaceutically acceptable salts thereof

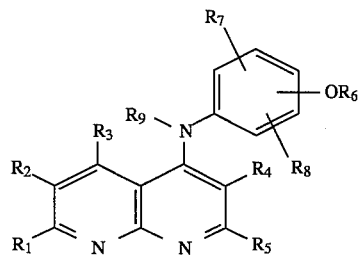

in which $R_1$ represents hydrogen, alkyl, hydroxy, carboxyalkenyl, alkoxycarbonylalkenyl, hydroxyalkyl, carboxyalkyl, alkoxycarbonylalkyl, alkoxy, halogenated alkyl, carboxy alkoxycarbonyl or alkanoylamino; $R_2$ represents hydrogen, halo, alkoxy, hydroxy, alkanoyloxy, or phenoxy; $R_3$ represents hydrogen or alkyl; $R_4$ represents hydrogen, halo, alkoxycarbonyl, a benzyloxycarbonyl, alkanoyl, benzoyl, carbamoyl, alkyl, carboxy, hydroxyalkyl or alkylthio; $R_5$ represents hydrogen or alkyl; $R_6$ represents hydrogen, alkyl [optionally substituted by one or more of the following: hydroxy, halo or an amino group of formula $-NR_{12}R_{13}$], a $C_{3-12}$ alicyclic hydrocarbon group, phenyl, (cycloalkyl)alkyl or benzyl; $R_7$ represents hydrogen, halo, trifluoromethyl, trifluoromethoxy, alkyl, carboxy, or alkoxy; $R_8$ represents hydrogen, halo, trifluoromethyl, trifluoromethoxy, alkyl or alkoxy; and $R_9$ represents hydrogen or alkyl; which are antirheumatic agents. Compositions containing these compounds and processes to make them are also disclosed.

16 Claims, No Drawings

AMINO NAPHTHYRIDINE COMPOUNDS AS ANTI-RHOUMATIC AGENTS

This application is the national phase of PCT/EP92/02901 filed Dec. 12, 1992.

The present invention relates to therapeutic agents, and in particular to substituted 4(5)-amino-1,8-naphthyridines, to processes for their preparation, to pharmaceutical compositions containing them and to their therapeutic activity as anti-rheumatic agents.

Rheumatoid arthritis is currently treated with anti-inflammatory agents, which alleviate the symptoms but do not affect the progression of the condition, or with disease-modifying antirheumatic drugs e.g. gold compounds, D-penicillamine, sulphasalazine, azathioprine and methotrexate. However, most disease-modifying antirheumatic drugs are associated with side-effects, often of a serious nature. This means that such drugs are often only used as a last resort in the most serious cases. Consequently a need exists for a less toxic, disease-modifying, antirheumatic drug which may be administered orally.

EP 0,361,177 discloses compounds of formula A

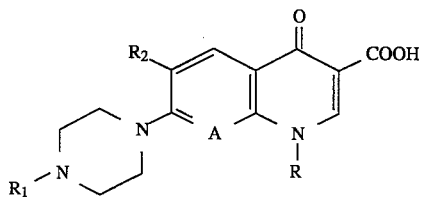

in which R represents alkyl, cyclopropyl, methylamino and p-fluorophenyl; $R_1$ represents hydrogen or a $C_{1-2}$ alkyl group; $R_2$ represents halo and A represents —CH— or a nitrogen atom. It is disclosed that these compounds may be used to treat rheumatoid arthritis by intraarticular administration.

Japanese patent application number 38774/69, publication number J47-29519 (1972) discloses ethyl 4-anilino-7-methyl-1,8-naphthyridine-3-carboxylate amongst a number of compounds which are prepared as intermediates for use in the preparation of anti-bacterial agents. It is suggested that these intermediates possess anti-bacterial and antiprotozoal activity but no results are given.

2-Diethylaminomethyl-4-(7'-methyl-1',8'-naphthyridin-4'-ylamino)phenol and 2-diethylaminomethyl-4-(1',8'-naphthyridin-4-ylamino)phenol are disclosed in the Australian Journal of Chemistry, 1984, 37, 1065 as having minimal anti-malarial activity.

The present invention relates to compounds of formula I

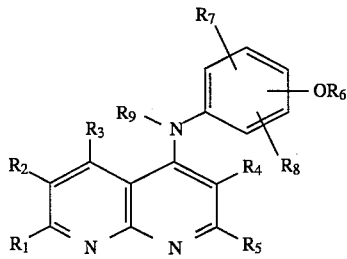

and pharmaceutically acceptable salts thereof in which $R_1$ represents hydrogen, a $C_{1-6}$ alkyl group, hydroxy, a carboxy $C_{2-4}$ alkenyl group, a $C_{2-6}$ alkoxycarbonyl $C_{2-4}$ alkenyl group, a hydroxy $C_{1-6}$ alkyl group, a carboxy $C_{1-4}$ alkyl group, a $C_{2-6}$ alkoxycarbonyl $C_{1-4}$ alkyl group, a $C_{1-6}$ alkoxy group, a halogenated $C_{1-6}$ alkyl group, a carboxy group, a $C_{2-6}$ alkoxycarbonyl group or a $C_{1-6}$ alkanoylamino group;

$R_2$ represents hydrogen, halo, a $C_{1-6}$ alkoxy group, hydroxy, a $C_{1-6}$ alkanoyloxy group, or a phenoxy group (which may be optionally substituted by a $C_{1-4}$ alkyl group, halo or a $C_{1-4}$ alkoxy group);

$R_3$ represents hydrogen or a $C_{1-4}$ alkyl group;

$R_4$ represents hydrogen, halo, a $C_{2-7}$ alkoxycarbonyl group, a benzyloxycarbonyl group (which may be optionally substituted by a $C_{1-4}$ alkyl group, halo or a $C_{1-4}$ alkoxy group), a $C_{1-6}$ alkanoyl group, a benzoyl group (which may be optionally substituted by a $C_{1-4}$ alkyl group, halo or a $C_{1-4}$ alkoxy group), carbamoyl, a $C_{1-6}$ alkyl group, a carboxy group, a $C_{1-6}$ hydroxyalkyl group or a $C_{1-6}$ alkylthio group;

$R_5$ represents hydrogen or a $C_{1-4}$ alkyl group;

$R_6$ represents hydrogen, a $C_{1-6}$ alkyl group [optionally substituted by one or more of the following: hydroxy, halo or an amino group of formula —$NR_{12}R_{13}$ (in which $R_{12}$ and $R_{13}$ independently represent hydrogen or a $C_{1-4}$ alkyl group or $R_{12}$ and $R_{13}$ together with the nitrogen atom to which they are attached represent a pyrrolidine ring, a morpholine ring or a piperidine ring)], a $C_{3-12}$ alicyclic hydrocarbon group, a phenyl group (which may be optionally substituted by a $C_{1-4}$ alkyl group, halo or a $C_{1-4}$ alkoxy group), a $C_{3-6}$ cycloalkyl $C_{1-4}$ alkyl group or a benzyl group (which may be optionally substituted by a $C_{1-4}$ alkyl group, halo or a $C_{1-4}$ alkoxy group);

$R_7$ represents hydrogen, halo, trifluoromethyl, trifluoromethoxy, a $C_{1-6}$ alkyl group, a carboxy group, or a $C_{1-6}$ alkoxy group;

$R_8$ represents hydrogen, halo, trifluoromethyl, trifluoromethoxy, a $C_{1-6}$ alkyl group or a $C_{1-6}$ alkoxy group; and $R_9$ represents hydrogen or a $C_{1-4}$ alkyl group.

It will be understood that a group containing a chain of 3 or more carbon atoms may be straight or branched, for example, propyl includes n-propyl and isopropyl and butyl includes n-butyl, sec-butyl, isobutyl and tert-butyl. Alicyclic groups may be bridged.

A preferred group of compounds of formula I, is represented by formula II

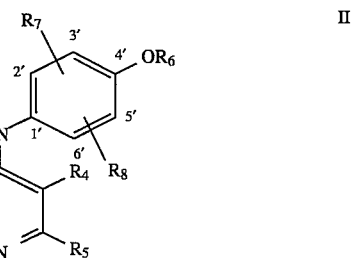

and pharmaceutically acceptable salts thereof in which $R_1$ represents hydrogen, a $C_{1-4}$ alkyl group (for example methyl, ethyl, propyl or butyl), hydroxy, a carboxy $C_{2-4}$ alkenyl group, a $C_{2-6}$ alkoxycarbonylvinyl group (for example methoxycarbonylvinyl, ethoxycarbonylvinyl or propoxycarbonylvinyl), an ω-hydroxy $C_{1-4}$ alkyl group (for example hydroxymethyl, 2-hydroxyethyl or 3-hydroxypropyl), a carboxy $C_{1-4}$ alkyl group (for example carboxymethyl, carboxyethyl or carboxypropyl), a $C_{2-6}$ alkoxycarbonyl $C_{1-4}$ alkyl group (for example methoxycarbonylmethyl, ethoxycarbonylpropyl or butoxycarbonylbutyl), a $C_{1-6}$ alkoxy group (for example methoxy, ethoxy, propoxy or butoxy) or a polyhalogenated $C_{1-4}$ alkyl group (for example trifluoromethyl or pentafluoroethyl);

$R_2$ represents hydrogen, halo (for example fluoro, bromo or chloro), a $C_{1-6}$ alkoxy group (for example methoxy, ethoxy, propoxy or butoxy) or hydroxy;

$R_3$ represents hydrogen;

$R_4$ represents hydrogen, halo (for example bromo or chloro), a $C_{2-5}$ alkoxycarbonyl group (for example methoxycarbonyl, ethoxycarbonyl, propoxycarbonyl or butoxycarbonyl), benzyloxycarbonyl, a $C_{2-6}$ alkanoyl group (for example acetyl, propionyl, butyryl or isobutyryl), carbamoyl, a $C_{1-4}$ alkyl group (for example methyl, ethyl, propyl or butyl), carboxy or an α-hydroxy $C_{1-6}$ alkyl group (for example hydroxymethyl, 1-hydroxyethyl, 1-hydroxypropyl or 1-hydroxybutyl);

$R_5$ represents hydrogen or a $C_{1-4}$ alkyl group (for example methyl, ethyl, propyl or butyl);

$R_6$ represents hydrogen, a $C_{1-6}$ alkyl group [optionally substituted by one or more of the following hydroxy, halo or an amino group of formula $NR_{12}R_{13}$ in which $R_{12}$ and $R_{13}$ independently represent hydrogen or a $C_{1-4}$ alkyl group] (for example $R_6$ represents methyl, ethyl, propyl, butyl, hydroxyethyl, hydroxypropyl, dihydroxypropyl, trifluoromethyl, diethylaminoethyl), a $C_{3-12}$ alicyclic hydrocarbon group (for example cyclopropyl, cyclobutyl, cyclopentyl, cyclohexyl, adamantyl), phenyl or benzyl;

$R_7$ represents hydrogen, halo (for example fluoro, bromo or chloro), trifluoromethyl, a $C_{1-4}$ alkyl group (for example methyl, ethyl, propyl or butyl), a carboxy group or a $C_{1-4}$ alkoxy group (for example methoxy, ethoxy, propoxy or butoxy);

$R_8$ represents hydrogen, halo (for example fluoro, bromo or chloro), trifluoromethyl, a $C_{1-4}$ alkyl group (for example methyl, ethyl, propyl or butyl) or a $C_{1-4}$ alkoxy group (for example methoxy, ethoxy, propoxy or butoxy);

$R_9$ represents hydrogen or a $C_{1-4}$ alkyl group (for example methyl, ethyl, propyl or butyl).

In preferred compounds of formula II, $R_1$ represents hydrogen, methyl, ethoxy, trifluoromethyl, hydroxy, 2-carboxyvinyl, 2-carboxyethyl or hydroxymethyl. More preferably $R_1$ represents hydrogen, methyl, ethoxy, trifluoromethyl or hydroxy. Most preferably $R_1$ represents methyl or ethoxy.

In preferred compounds of formula II, $R_2$ represents hydrogen, methoxy, ethoxy, propoxy or bromo. More preferably $R_2$ represents hydrogen, ethoxy or bromo. Most preferably $R_2$ represents hydrogen or ethoxy.

In preferred compounds of formula II, $R_3$ represents hydrogen.

In preferred compounds of formula II, $R_4$ represents hydrogen, bromo, ethoxycarbonyl, 1-butyryl, carboxy, carbamoyl, hydroxymethyl or 1-hydroxybutyl. More preferably $R_4$ represents hydrogen, ethoxycarbonyl or 1-butyryl. Most preferably $R_4$ represents hydrogen or ethoxycarbonyl.

In preferred compounds of formula II, $R_5$ represents hydrogen or methyl. More preferably $R_5$ represents hydrogen.

In preferred compounds of formula II, $R_6$ represents hydrogen, methyl, ethyl, 1-adamantyl, phenyl, 2-(diethylamino)ethyl, 2-hydroxyethyl, 2,3-dihydroxypropyl, trifluoromethyl or benzyl. More preferably $R_6$ represents hydrogen, methyl, phenyl, 2-(diethylamino)ethyl, 2-hydroxyethyl, 2,3-dihydroxypropyl. Most preferably $R_6$ represents hydrogen, methyl or 2-hydroxyethyl.

In preferred compounds of formula II, $R_7$ represents hydrogen, 2'-methyl, 3'-methyl, 3'-methoxy, 3'-chloro or 3'-carboxy. More preferably $R_7$ represents hydrogen, 2'-methyl, 3'-methyl or 3'-methoxy. Most preferably $R_7$ represents hydrogen or 3'-methyl.

In preferred compounds of formula II, $R_8$ represents hydrogen, 5'-methyl, 5'-methoxy or 5'-chloro. More preferably $R_8$ represents hydrogen, 5'-methyl or 5'-methoxy. Most preferably $R_8$ represents hydrogen or 5'-methyl.

In preferred compounds of formula II, $R_9$ represents hydrogen or methyl. More preferably $R_9$ represents hydrogen.

One group of more preferred compounds of formula I is represented by formula II in which $R_1$ represents hydrogen, a $C_{1-4}$ alkyl group or 2-carboxyvinyl;

$R_2$ represents a $C_{2-4}$ alkoxy group;

$R_3$ represents hydrogen;

$R_4$ represents a $C_{3-4}$ alkoxycarbonyl group;

$R_5$ represents hydrogen;

$R_6$ represents a $C_{1-4}$ alkyl group, phenyl, benzyl, trifluoromethyl, 2-hydroxyethyl, 2-(diethylamino)ethyl, 2,3-dihydroxypropyl;

$R_7$ represents hydrogen or 2'-methyl and $R_8$ and $R_9$ represent hydrogen.

A second group of more preferred compounds of formula I is represented by formula II in which $R_1$ represents hydrogen, hydroxy, ethoxy or trifluoromethyl;

$R_2$ represents hydrogen;

$R_3$ represents hydrogen;

$R_4$ represents a $C_{3-4}$ alkoxycarbonyl group;

$R_5$ represents hydrogen;

$R_6$ represents a $C_{1-4}$ alkyl group (which may be optionally substituted by one or more of the following: hydroxy, halo or an amino group of formula —$NR_{12}R_{13}$ in which $R_{12}$ and $R_{13}$ independently represents hydrogen or a $C_{1-4}$ alkyl group); and $R_7$, $R_8$ and $R_9$ each represent hydrogen.

A third group of more preferred compounds of formula I is represented by formula II in which $R_1$ represents a $C_{1-4}$ alkyl group;

$R_2$ represents a $C_{2-4}$ alkoxy group;

$R_3$, $R_4$, $R_5$ and $R_6$ represent hydrogen;

$R_7$ represents hydrogen or a $C_{1-4}$ alkyl group;

$R_8$ represents hydrogen or a $C_{1-4}$ alkyl group; and $R_9$ represents hydrogen.

Specific compounds of formula I are:

Ethyl 6-ethoxy-4-(4-methoxyanilino)-7-methyl-1,8-naphthyridine-3-carboxylate

3-Ethoxy-5-(4-methoxyanilino)-2-methyl-1,8-naphthyridine

Ethyl 4-(4-methoxyanilino)-7-trifluoromethyl-1,8-naphthyridine-3-carboxylate

Ethyl 6-ethoxy-4-(4-methoxyanilino)-1,8-naphthyridine-3-carboxylate

3-Butyryl-6-ethoxy-4-(4-methoxyanilino)-7-methyl-1,8-naphthyridine

Ethyl 7-ethoxy-4-(4-methoxyanilino)-1,8-naphthyridine-3-carboxylate

Ethyl 6-bromo-4-(4-methoxyanilino)-7-1,8-naphthyridine-3-carboxylate
3-Bromo-5-(4-methoxyanilino)-2-methyl-1,8-naphthyridine
Ethyl 6-ethoxy-4-[4-(2-hydroxyethoxy)anilino]-7-methyl-1,8-naphthyridine-3-carboxylate
Ethyl 6-ethoxy-4-(4-methoxy-2-methylanilino)-7-methyl-1,8-naphthyridine-3-carboxylate
3-Ethoxy-5-(4-methoxy-2-methylanilino)-2-methyl-1,8-naphthyridine
4-[4-(2-Diethylaminoethoxy)anilino]-6-ethoxy-7-methyl-1,8-naphthyridine
4-(6-Ethoxy-7-methyl-1,8-naphthyridin-4-ylamino)-2,6-xylenol
5-[4-(1-Adamantyloxy)anilino]-3-ethoxy-2-methyl-1,8-naphthyridine
3-Ethoxy-5-(2-methoxyanilino)-2-methyl-1,8-naphthyridine
Ethyl 6-ethoxy-4-(4-ethoxyanilino)-7-methyl-1,8-naphthyridine-3-carboxylate
Ethyl 6-ethoxy-7-methyl-4-(4-trifluoromethoxyanilino)-1,8-naphthyridine-3-carboxylate
Ethyl 4-(4-benzyloxyanilino)-6-ethoxy-7-methyl-1,8-naphthyridine-3-carboxylate
Ethyl 4-[4-(2,3-dihydroxypropoxy)anilino]-6-ethoxy-7-methyl-1,8-naphthyridine-3-carboxylate
Ethyl 6-ethoxy-4-(4-hydroxy-3-methylanilino)-7-methyl-1,8-naphthyridine-3-carboxylate
Ethyl 4-[4-(2-diethylaminoethoxy)anilino]-6-ethoxy-7-methyl-1,8-naphthyridine-3-carboxylate
Ethyl 6-ethoxy-4-(4-methoxy-3,5-dimethylanilino)-7-methyl-1,8-naphthyridine-3-carboxylate
2,6-Dichloro-4-(6-ethoxy-7-methyl-1,8-naphthyridin-4-ylamino)phenol
6-Ethoxy-4-(4-methoxyanilino)-7-methyl-1,8-naphthyridine-3-carboxamide
Ethyl 4-(4-methoxyanilino)-7-methyl-6-propoxy-1,8-naphthyridine-3-carboxylate
Ethyl 6-methoxy-4-(4-methoxyanilino)-7-methyl-1,8-naphthyridine-3-carboxylate
6-Bromo-3-ethoxy-5-(4-methoxyanilino)-2-methyl-1,8-naphthyridine
5-(6-Ethoxy-3-ethoxycarbonyl-7-methyl-1,8-naphthyridin-4-ylamino)salicylic acid
3-Ethoxy-5-(4-methoxyanilino)-2,7-dimethyl-1,8-naphthyridine
3-Ethoxy-5-(4-methoxyanilino)-2,6-dimethyl-1,8-naphthyridine
Ethyl 6-ethoxy-7-methyl-4-(3,4,5-trimethoxyanilino)-1,8-naphthyridine-3-carboxylate
3-[4-(6-Ethoxy-7-methyl-1,8-naphthyridin-4-ylamino)phenoxy]propane-1,2-diol
3-Ethoxy-2-methyl-5-(4-phenoxyanilino)-1,8-naphthyridine
Ethyl 6-ethoxy-7-methyl-4-(4-phenoxyanilino)-1,8-naphthyridine-3-carboxylate
4-(6-Ethoxy-7-methyl-1,8-naphthyridine-4-ylamino)phenol
Ethyl 6-ethoxy-4-(4-methoxy-N-methylanilino)-7-methyl-1,8-naphthyridine-3-carboxylate
6-Ethoxy-4-(4-methoxyanilino)-7-methyl-1,8-naphthyridin-3-ylmethanol
3-[3-Ethoxy-5-(4-methoxyanilino)-1,8-naphthyridin-2-yl]acrylic acid
3-[3-Ethoxy-6-ethoxycarbonyl-5-(4-methoxyanilino)-1,8-naphthyridin-2-yl]acrylic acid
3-[3-Ethoxy-6-ethoxycarbonyl-5-(4-methoxyanilino)-1,8-naphthyridin-2-yl]propionic acid 6-Ethoxy-4-(4-methoxyanilino)-7-methyl-1,8-naphthyridine-3-carboxylic acid
Ethyl 4-[4-methoxyanilino]-7-oxo-7,8-dihydro-1,8-naphthyridine-3-carboxylate
5-(4-Methoxyanilino)-1,8-naphthyridin-2-ylmethanol
1-[6-Ethoxy-4-(4-methoxyanilino)-7-methyl-1,8-naphthyridin-3-yl]butan-1-ol
6-Hydroxy-4-(4-methoxyanilino)-7-methyl-1,8-naphthyridine-3-carboxylic acid and pharmaceutically acceptable salts thereof, in the form of individual enantiomers, racemates or other mixtures of enantiomers.

When a compound of formula I contains a single chiral centre it may exist in two enantiomeric forms. The present invention includes individual enantiomers and mixtures of those enantiomers. The enantiomers may be obtained by methods known to those skilled in the art. Such methods typically include resolution via formation of diastereoisomeric salts or complexes which may be separated, for example, by crystallisation; resolution via formation of diastereoisomeric derivatives or complexes which may be separated, for example, by crystallisation, gas-liquid or liquid chromatography; selective reaction of one enantiomer by reaction with an enantiomer-specific reagent, for example, enzymatic esterification, oxidation or reduction, followed by separation of the modified and unmodified enantiomers; or gas-liquid or liquid chromatography in a chiral environment, for example on a chiral support such as silica with a bound chiral ligand or in the presence of a chiral solvent. It will be appreciated that where the desired enantiomer is converted into another chemical entity by one of the separation processes described above, a further step will subsequently be required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to those skilled in the art, for example, chromatography or crystallisation and the individual enantiomers within each pair may be separated as described above. The present invention includes each diastereoisomer of compounds of formula I or II and mixtures thereof.

Certain compounds of formula I may exist in different tautomeric forms which fall within the scope of the present invention.

Some compounds of formula I may exist in the form of solvates, for example, hydrates, which also fall within the scope of the present invention.

The compounds of formula I may form organic or inorganic salts, for example, the compounds of formula I may form acid addition salts with inorganic or organic acids, e.g. hydrochloric acid, hydrobromic acid, fumaric acid, tartaric acid, citric acid, sulphuric acid, hydriodic acid, maleic acid, acetic acid, succinic acid, benzoic acid, pamoic acid, palmitic acid, dodecanoic acid and acidic amino acids such as glutamic acid. Some compounds of formula I may form base addition salts, for example, with alkali metals for example sodium hydroxide, or with amino acids for example, lysine or arginine. It will be appreciated that such salts, provided they are pharmaceutically acceptable may be used in therapy in place of the corresponding compounds of formula I. Such salts are prepared by reacting the compound of formula I with a suitable acid or base in a conventional manner. Such salts may also exist in form of solvates (for example, hydrates).

Certain compounds of formula I may exist in more than one crystal form and the present invention includes each crystal form and mixtures thereof.

The present invention also provides pharmaceutical compositions containing a therapeutically effective amount of a compound of formula I together with a pharmaceutically acceptable diluent or carrier. Such pharmaceutical formulations may be used in the treatment of rheumatic diseases for example rheumatoid arthritis or osteoarthritis.

As used hereinafter, the term "active compound" denotes a 1,8-naphthyridine of formula I. In therapeutic use, the active compound may be administered orally, rectally, parenterally, topically, ocularly, aurally, nasally, intravaginally or to the buccal cavity, to give a local and/or systemic effect. Thus the therapeutic compositions of the present invention may take the form of any of the known pharmaceutical compositions for such methods of administration. The compositions may be formulated in a manner known to those skilled in the art so as to give a controlled release, for example rapid release or sustained release, of the compounds of the present invention. Pharmaceutically acceptable carriers suitable for use in such compositions are well known in the art of pharmacy. The compositions of the invention may contain 0.1–90% by weight of active compound. The compositions of the invention are generally prepared in unit dosage form. Preferably the unit dosage of active ingredient is 1– 500 mg. The excipients used in the preparation of these compositions are the excipients known in the pharmacist's art.

Compositions for oral administration are preferred compositions of the invention and there are known pharmaceutical forms for such administration, for example tablets, capsules, granules, syrups and aqueous or oily suspensions.

Tablets may be prepared from a mixture of the active compound with fillers such as lactose or calcium phosphate, disintegrating agents, for example maize starch, lubricating agents, for example magnesium stearate, binders for example microcrystalline cellulose or polyvinyl pyrrolidone and other optional ingredients known in the art to permit tableting the mixture by known methods. The tablets may, if desired, be coated using known methods and excipients which may include enteric coating using for example hydroxypropylmethylcellulose phthalate. The tablets may be formulated in a manner known to those skilled in the art so as to give a sustained release of the compounds of the present invention. Such tablets may, if desired, be provided with enteric coatings by known methods, for example by the use of cellulose acetate phthalate.

Similarly, capsules, for example hard or soft gelatin capsules, containing the active compound with or without added excipients, may be prepared by known methods and, if desired, provided with enteric coatings in a known manner. The tablets and capsules may conveniently each contain 0.1 to 1000 mg (for example 10 mg, 50 mg, 100 mg, 200 mg, 400 mg or 800 mg) of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example sunflower oil.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Compositions for topical administration are also preferred compositions of the invention. The pharmaceutically active compound may be dispersed in a pharmaceutically acceptable cream, ointment or gel. A suitable cream may be prepared by incorporating the active compound in a topical vehicle such as petrolatum and/or light liquid paraffin, dispersed in an aqueous medium using surfactants. An ointment may be prepared by mixing the active compound with a topical vehicle such as a mineral oil, petrolatum and/or a wax e.g. paraffin wax or beeswax. A gel may be prepared by mixing the active compound with a topical vehicle comprising a gelling agent e.g. basified Carbomer BP, in the presence of water. Topically administrable compositions may also comprise a matrix in which the pharmaceutically active compounds of the present invention are dispersed so that the compounds are held in contact with the skin in order to administer the compounds transdermally. A suitable transdermal composition may be prepared by mixing the pharmaceutically active compound with a topical vehicle, such as described above, together with a potential transdermal accelerant such as dimethyl sulphoxide or propylene glycol.

Compositions of the invention suitable for rectal administration are known pharmaceutical forms for such administration, for example suppositories with hard fat, synthetic glycerides or polyethylene glycol bases.

Compositions of the invention suitable for parenteral administration are known pharmaceutical forms for such administration, for example sterile suspensions or sterile solutions in a suitable solvent.

Compositions of the invention suitable for inhalation via the mouth and/or the nose are the known pharmaceutical forms for such administration, for example aerosols, nebulised solutions or powders. Metered dose systems, known to those skilled in the art, may be used.

Compositions suitable for application to the buccal cavity include slow dissolving tablets, troches, chewing gum, gels, pastes, powders, mouthwashes or rinses.

The compounds of the present invention may also be administered by continuous infusion either from an external source, for example by intravenous infusion, or from a source of the compound placed within the body. Internal sources include implanted reservoirs containing the compound to be infused which is continuously released for example by osmosis and implants which may be a) liquid such as an oily solution or suspension of the compound to be infused for example in the form of a very sparingly water-soluble derivative such as a dodecanoate salt or b) solid in the form of an implanted support for example of a synthetic resin of waxy material for the compound to be infused. The support may be a single body containing all the compound or a series of several bodies each containing part of the compound to be delivered.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients, for example, a non-steroidal antiinflammatory agent e.g. ibuprofen, S(+)-ibuprofen, flurbiprofen or S(+)-flurbiprofen, an analgesic or an antipyretic agent.

The compounds of formula I are indicated for use as anti-rheumatic agents by their activity demonstrated by means of tests on standard laboratory animals. Such tests include, for example, the oral administration of compounds of formula I to mice with experimental antigen-induced arthritis. Compounds of formula I are suitable for use in treating rheumatic diseases for example rheumatoid arthritis, osteoarthritis, osteoporosis, crystal arthropathies (e.g. gout), reactive arthritis, ankylosing spondylitis or psoriatic arthropathy.

Compounds of formula I may also be suitable for the treatment of diseases of the oral cavity for example periodontitis, gingivitis and alveolar bone resorption.

Accordingly, in a further aspect, the present invention also includes a method of treating rheumatic diseases, particularly rheumatoid arthritis and osteoarthritis, comprising the administration of a therapeutically effective amount of a compound of formula I to a mammal in need thereof. Compounds of formula I may also be administered in a prophylactic manner to mammals, particularly humans who have been identified as being susceptible to arthritic diseases. Whilst the precise amount of active compound administered will depend on a number of factors, for example the age of the patient, the severity of the condition and the past medical history and always lies within the sound discretion of the administering physician, a suitable dose for oral administration to mammals, including humans, is generally within the range 0.01–80 mg/kg/day, more usually 0.2–40 mg/kg/day given in single or divided doses. For parenteral administration, a suitable dose is generally within the range 0.001–80 mg/kg/day, more usually 0.2–40 mg/kg/day given in single or divided doses or by continuous infusion. A suitable preparation for topical administration generally contains the active ingredient within the range 0.01–20% by weight, more usually 0.05–5% by weight. Oral administration is preferred.

The pharmaceutical compositions containing a therapeutically effective amount of a compound of formula I may be used to treat rheumatic diseases such as rheumatoid arthritis and osteoarthritis. In such treatment the amount of the compound of formula I administered per day is in the range 0.1 to 6000 mg.

In yet another aspect, the present invention provides the use of a compound of formula I in the manufacture of a medicament for use in the treatment of a rheumatic disease such as rheumatoid arthritis and osteoarthritis.

Processes for the preparation of compounds of formula I will now be described. These processes form a further aspect of the present invention.

Compounds of formula I in which $R_1$ represents a carboxy $C_{2-4}$ alkyl group may be prepared by reducing a compound of formula I in which $R_1$ represents a carboxy $C_{2-4}$ alkenyl group, for example with a reducing agent, e.g. hydrogen in the presence of a catalyst e.g. palladium.

Compounds of formula I in which $R_1$ represents hydroxy may be prepared by hydrolysis of a compound of formula I in which $R_1$ represents a $C_{1-6}$ alkoxy group, for example using a base e.g. sodium hydroxide.

Compounds of formula I in which $R_4$ represents an α-hydroxy $C_{1-6}$ alkyl group may be prepared by reducing a compound of formula I in which $R_4$ represents a $C_{2-7}$ alkoxycarbonyl group or a $C_{1-6}$ alkanoyl group, by methods known to those skilled in the art, for example using lithium aluminium hydride or lithium triethylborohydride.

Compounds of formula I in which $R_2$ represents hydroxy may be prepared by reacting a compound of formula I in which $R_2$ represents a $C_{1-6}$ alkoxy group with a de-alkylating agent for example aluminium chloride.

Compounds of formula I in which $R_4$ represents carboxy may be prepared by hydrolysis of compounds of formula I in which $R_4$ represents a $C_{2-6}$ alkoxycarbonyl group by methods known to those skilled in the art, for example using an acid e.g. hydrochloric acid or a base e.g. sodium hydroxide.

Compounds of formula I in which $R_1$ represents an ω-hydroxy $C_{1-6}$ alkyl may be prepared by reducing a compound of formula I in which $R_1$ represents a $C_{2-6}$ alkoxycarbonyl group or a $C_{2-6}$ alkoxycarbonyl $C_{1-4}$ alkyl group by methods known to those skilled in the art for example using lithium aluminium hydride or lithium triethylborohydride.

Compounds of formula I in which $R_1$ represents a carboxyvinyl group may be prepared by reacting compounds of formula I in which $R_1$ represents methyl with glyoxylic acid for example by heating together optionally in the presence of a catalyst e.g. trifluoroacetic acid.

Compounds of formula I in which $R_6$ represents a group other than hydrogen may be prepared by reacting a compound of formula I in which $R_6$ represents hydrogen with a compound of formula $R_6L$ (XVI) in which L represents a leaving group for example halo, for example by heating, optionally in the presence of an inert organic liquid which is preferably a solvent for the reactants e.g. N,N-dimethylformamide at a temperature in the range 0°–150° C., preferably in the range 30°–120° C., at atmospheric pressure, preferably in the presence of a base for example sodium hydride.

Compounds of formula I may be prepared by reacting a compound of formula III

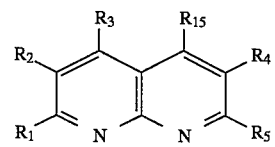

III in which $R_{15}$ represents a leaving group, including halo, e.g. bromo or chloro; mercapto or methylthio with a compound of formula IV

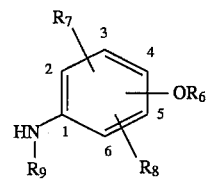

IV or a salt thereof by heating, optionally in the presence of an inert organic liquid which is preferably a solvent for the reactants, e.g. an alcohol or an ether, at a temperature in the range 0°–150° C., preferably in the range 30°–120° C., at atmospheric pressure, optionally in the presence of an acid, for example hydrochloric acid, or a base, for example sodium carbonate or sodium bicarbonate.

Compounds of formula I in which $R_1$ represents a $C_{1-6}$ alkoxy group may be prepared by reacting a compound of formula XVII

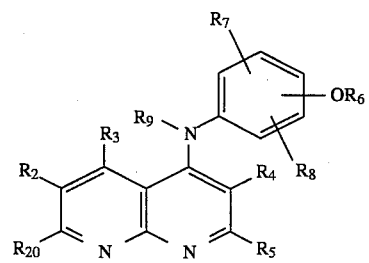

XVII in which $R_{20}$ represents a leaving group, for example halo, with an alkali metal $C_{1-6}$ alkoxide, by heating optionally in the presence of an inert organic liquid which is preferably a solvent for the reactants, for example an alcohol, at a temperature in the range 50°–250° C. preferably 150°–200° C. preferably in a sealed vessel under pressure.

Compounds of formula I in which $R_1$ represents hydroxy may be prepared by displacing $R_{20}$ from a compound of formula XVII, in which $R_{20}$ represents a leaving group, for example halo, with a hydroxy group, for example by reacting with an alkali metal hydroxide in the presence of an inert organic liquid or by hydrolysis using an aqueous acid or base, at a temperature in the range 0°–200° C.

Compounds of formula III in which $R_{15}$ represents halo may be prepared by reacting compounds of formula V

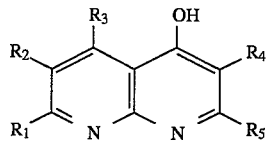

V with a halogenating agent for example phosphorus oxychloride or phosphorus oxybromide at a temperature in the range 0°–150° C., preferably 20°–100° C., optionally in the presence of an inert organic liquid which is preferably a solvent for the reactants. Compounds of formula III in which $R_{15}$ represents mercapto or methylthio may be prepared from compounds of formula V by methods known to those skilled in the art.

Compounds of formula V in which $R_1$ represents hydrogen may be prepared by the thermal decarboxylation of compounds of formula VI

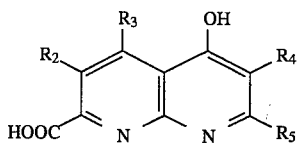

VI for example by heating at a temperature in the range 100°–350° C. in a suitable organic liquid e.g. diphenyl ether, quinoline or liquid petrolatum.

Compounds of formula V in which $R_1$ represents a substituent other than hydrogen may be prepared by heating compounds of formula VII

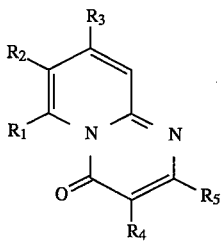

VII in which $R_1$ represents a substituent other than hydrogen in the presence of a suitable solvent, for example diphenyl ether or liquid petrolatum at a temperature in the range 150° to 350° C.

Compounds of formula V in which $R_4$ represents hydrogen may be prepared by heating compounds of formula V in which $R_4$ represents $COOR_{16}$ and $R_{16}$ represents hydrogen or a $C_{1-4}$ alkyl group, with aqueous sodium hydroxide solution in a sealed vessel or by thermal decarboxylation of compounds of formula V in which $R_{16}$ represents hydrogen optionally in the presence of an organic liquid, for example quinoline or liquid petrolatum.

Compounds of formula VI may be prepared by oxidising compounds of formula V in which $R_1$ represents a $C_{1-6}$ alkyl group, for example with selenium dioxide, or by oxidising compounds of formula V in which $R_1$ represents a carboxyvinyl group for example with potassium permanganate.

Compounds of formula VII may be prepared by heating compounds of formula VIII

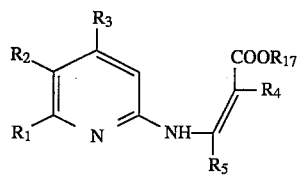

VIII in which $R_{17}$ represents a $C_{1-4}$ alkyl group in the presence of a suitable solvent, for example diphenyl ether or liquid petrolatum at a temperature in the range 150° to 350° C., or by reacting compounds of formula VIII with phosphorus oxychloride in the presence of polyphosphoric acid.

Compounds of formula VIII, in which $R_1$ represents a substituent as defined above, other than hydrogen, may be heated in the presence of an organic liquid, for example diphenyl ether or liquid petrolatum at a temperature in the range of 150° to 350° C. to produce compounds of formula V.

Compounds of formula VIII in which $R_5$ represents hydrogen may be prepared by reacting a compound of formula IX

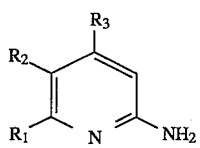

IX with a compound of formula X

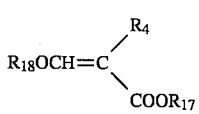

X in which $R_{17}$ or $R_{18}$ independently represent a $C_{1-4}$ alkyl group or with a compound of formula XI

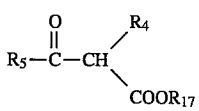

XI or a salt thereof, e.g. the sodium salt, in which $R_{17}$ represents a $C_{1-4}$ alkyl group, in the presence of a suitable solvent, for example ethanol, at a temperature in the range 50° to 200° C.

Compounds of formula VIII in which $R_5$ represents hydrogen may also be prepared by reacting a compound of formula IX with a tri($C_{1-4}$ alkyl)orthoformate and a compound of formula $R_4CH_2CO_2R_{17}$, for example by heating, optionally in the presence of a solvent for example acetic anhydride and/or a Lewis acid catalyst for example zinc chloride.

Compounds of formulae IX, X and XI may be prepared by methods known to those skilled in the art.

Compounds of formula XII

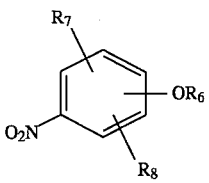

XII may be reduced for example, by heating in the presence of reduced iron powder and dilute acid, to prepare compounds of formula IV, in which $R_9$ represents hydrogen.

Compounds of formula XII in which $R_6$ represents an optionally substituted $C_{1-6}$ alkyl group or an optionally substituted phenyl group and $OR_6$ is located ortho or para to the nitro group may be prepared by reacting a compound of formula XIII

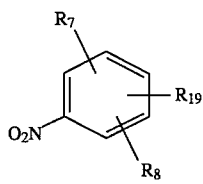

XIII in which $R_{19}$ represents halo and is located ortho or para to the nitro group, respectively, with a salt of formula XIV $$MOR_6 \quad\quad XIV$$

in which $R_6$ represents an optionally substituted $C_{1-6}$ alkyl group or a phenyl group, which may be optionally substituted, and M represents an alkali metal, for example sodium or potassium, for example by heating, optionally in the presence of an organic liquid, which is preferably a solvent for the reactants, for example $R_6OH$.

Compounds of formula XII in which $R_6$ represents an optionally substituted alkyl group may be prepared by alkylating a compound of formula XV

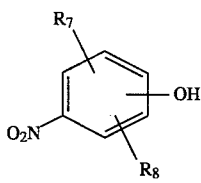

XV by methods known to those skilled in the art for example by reaction with a compound of formula $R_6L$ (XVI) in which L represents a leaving group for example halo.

Compounds of formulae XIII, XIV, XV and XVI may be prepared by methods known to those skilled in the art.

Compounds of formula XVII may be prepared by reacting a compound of formula XVIII

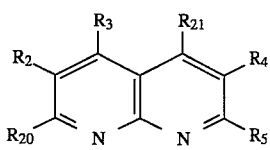

XVIII in which $R_{21}$ represents halo, for example chloro or bromo, with a compound of formula IV using conditions analogous to those described for the preparation of compounds of formula I from a compound of formula III and a compound of formula IV.

Compounds of formula XVIII may be prepared by processes analogous to those described for the preparation of compounds of formula III.

Certain intermediate compounds of formulae III–X inclusive are believed to be novel compounds. All novel compounds herein form a further aspect of the invention.

The therapeutic activity of the compounds of the present invention has been demonstrated by tests which include the oral administration of the compounds to mice with experimental antigen-induced arthritis. The compounds showed activity in the following test:

Female BALB/c mice, 8 weeks of age were used: each control group contained either 35 or 80 mice and each test group contained either 13 or 20 mice respectively. The mice were sensitised by subcutaneous injection into the flank with an emulsion (0.1 ml) consisting of a solution of methylated bovine serum albumin (m-BSA) (0.1 mg) in sterile aqueous sodium chloride solution (0.05 ml; 0.15M) and Complete Adjuvant (0.05 ml) containing, in total, Mycobacterium (0.075 mg). Simultaneously each mouse was injected intraperitoneally with an aqueous suspension of heat killed Bordetella Pertussis (0.05 ml; $2 \times 10^9$ organisms). Identical injections were administered after 7 days. After a further 14 days the left knee-joint of each mouse was injected with a solution of m-BSA (0.1 mg) in aqueous sodium chloride solution (0.01 ml; 0.15M) (intra-articular challenge). This procedure induced a chronic erosive arthritis restricted to the challenged joint.

The test compounds were suspended in a vehicle of aqueous carboxymethyl cellulose solution (0.25% w/v) containing TWEEN®80 (1.5% w/v) at varying dosages and 0.1 ml was administered to each test mouse by gastric incubation. The control mice received the vehicle with no test compound. Administration occurred daily for 28 days commencing 14 days after intra-articular challenge. After 42 days the test was terminated and the animals were killed using a rising concentration of carbon dioxide and the arthritic hind leg removed.

The femur and tibia were cut midway along their length and the knee-joint trimmed free of skin and musculature. The arthritic joints were placed in perforated plastic holders and fixed in 10% formol saline for at least 48 hours. They were then decalcified in 5% formic acid for 72 hours with constant agitation (replacing the formic acid after the first 24 hours), washed in water, dehydrated in alcohol and embedded in paraffin wax. The joints were sectioned in the sagittal plane at 5 µm and stained with Van Gieson's stain. Each joint was sectioned at two levels.

The severity of arthritis was assessed by examination of the prepared sections. Synovitis and pannus formation were graded on a 0–5 scale, by a skilled operator, according to the degree of synovial lining cell hypertrophy and hyperplasia, infiltration of the synovium by lymphocytes, plasma cells, monocytes/macrophages, fibroblasts and polymorphonuclear (PMN) leukocytes and the degree of pannus formation. Erosions of cartilage and bone were also graded on a 0–5 scale, by a skilled operator, the score reflecting the proportion of articular surface eroded as well as the depth of the erosions. Using the combined data the drug effects were expressed as the percentage change in the mean scores for synovitis and erosions compared to those of the control group. The data were then analysed using the Mann-Whitney U-test.

Those compounds which induced a statistically significant suppression of erosions or synovitis at a dosage of 100 mg/kg or below were deemed to be active. The results obtained are given in the Examples.

As an alternative to histological assessments, analysis of macerated specimens of tibial epiphyses using an image analysis system, may be used to assess the extent of hard tissue erosions. Active compounds are those which significantly reduce these erosions.

The invention is illustrated by the following non-limitative Examples in which parts and percentages are by weight and compositions of mixed solvents are given by volume. Novel compounds were characterised by elemental analysis and one or more of the following spectroscopic techniques: nuclear magnetic resonance, infra-red and mass spectroscopy.

In the Examples the following abbreviations are used: IMS=industrial methylated spirit and DMF=N,N-dimethylformamide.

Unless otherwise stated, the starting materials used in the Examples were commercially available and may be obtained by reference to the Fine Chemicals Directory.

Preparation of Starting Materials and Intermediates

Example A1 a) Sodium metal (46.2 g) was dissolved in absolute ethanol (1 l) with stirring under nitrogen. 3-Hydroxy-2-methylpyridine (200 g prepared as described in C.A. 48, P4597 h) was added. The mixture was stirred at ambient temperature for 30 minutes and then a solution of bromoethane (350 ml) in absolute ethanol (100 ml) was added. The mixture was boiled under reflux for 5 hours then cooled and filtered. The filtrate was evaporated and the residue partitioned between dichloromethane and water. The organic layer was separated off and the aqueous layer extracted with dichloromethane. The combined organic extracts were dried and evaporated. The residue was distilled to give 3-ethoxy-2-methylpyridine b.p. 80°–84° C. (20 mmHg).

b) 3-Ethoxy-2-methylpyridine (132.5 g) was added dropwise to concentrated sulphuric acid (530 ml) with stirring and cooling to keep the mixture below 10° C. A mixture of concentrated nitric acid (81 ml) and concentrated sulphuric acid (97 ml) was added dropwise over 4 hours, keeping the temperature below 5° C. The reaction mixture was allowed to warm up slowly to ambient temperature and then added in portions to ice/water (2.5 l). The solid was collected by filtration, washed with water and dried under vacuum at 50° C: to give 3-ethoxy-2-methyl-6-nitropyridine, m.p. 82°–84° C.

c) The nitropyridine above (176 g), IMS (1.6 l), reduced iron powder (179 g) and water (350 ml) were boiled under reflux. Heating was discontinued while concentrated hydrochloric acid (67 ml) was carefully added dropwise over 20 minutes. The mixture was boiled under reflux for 1.75 hours then cooled and filtered through a filtration aid. The filtrate was evaporated under reduced pressure. Water was added to the residue and the mixture basified with 5M sodium hydroxide. Extractive work-up (dichloromethane) gave 5-ethoxy-6-methylpyridin-2-amine, m.p. 93°–96° C.

d) A mixture of the amine from (c) above (138 g) and diethyl ethoxymethylenemalonate (196 g) in IMS (190 ml) was boiled under reflux for 3 hours. The mixture was cooled and filtered to give diethyl 2-(5-ethoxy-6-methylpyrid-2-ylaminomethylene)malonate, m.p. 132°–138° C.

e) The malonate (118.3 g) from (d) above was added to boiling diphenyl ether (1.5 l) over 10 minutes with stirring while allowing the ethanol formed to be removed by downward distillation. The mixture was boiled under reflux for 1.5 hours then cooled and diluted with petroleum ether b.p. 60°–80° C. (1.5 l). The solid was collected by filtration and washed with petroleum ether b.p. 60°–80° C. to give ethyl 6-ethoxy-4-hydroxy-7-methyl-1,8-naphthyridine-3-carboxylate, m.p. 255°–258° C.

f) A mixture of ethyl 6-ethoxy-4-hydroxy-7-methyl-1,8-naphthyridine-3-carboxylate (7.5 g), sodium hydroxide pellets (1.2 g) and water (20 ml) was heated at 180° C. with stirring in a sealed reaction vessel for 16 hours. The mixture was cooled to ambient temperature, filtered and the residue washed with water to give, after drying, 6-ethoxy-7-methyl-1,8-naphthyridin-4-ol, m.p. 278°–282° C. (with decomposition).

Example A2 a) A mixture of 2-chloro-6-trifluoromethylpyridine (20.0 g), cuprous chloride (0.2 g) and ammonia (specific gravity 0.88, 75 ml) was heated at 170° C. in a pressure vessel for 18 hours. After cooling to ambient temperature, the mixture was extracted with dichloromethane (300 ml). The organic extract was dried and evaporated to give 6-trifluoromethylpyridin-2-amine, m.p. 74°–79° C.

b) A mixture of 6-trifluoromethylpyridin-2-amine (17.2 g) and diethyl ethoxymethylenemalonate (22.9 g) was heated at 95° C., under vacuum for 8 hours. The mixture was cooled and diluted with petroleum ether b.p. 60°–80° C. (50 ml). The mixture was filtered and the residue was recrystallised from IMS to give diethyl 2-(6-trifluoromethyl-2-pyridylaminomethylene)malonate, m.p. 125°–128° C.

c) The above malonate (22.55 g) was added dropwise with stirring to boiling diphenyl ether (250 ml) under reflux. The mixture was boiled for 2 hours, then cooled and diluted with petroleum ether b.p. 60°–80° C. The solid was collected by filtration to give ethyl 4-hydroxy-7-trifluoromethyl-1,8-naphthyridine-3-carboxylate, m.p. >250° C.

Example A3 a) A mixture of ethyl 6-ethoxy-4-hydroxy-7-methyl-1,8-naphthyridine-3-carboxylate (2.8 g), glyoxylic acid monohydrate (1.5 g) acetic acid (20 ml) and trifluoroacetic acid (10 ml) was heated at 90°–95° C. for 2 hours, with stirring. The mixture was evaporated down under reduced pressure. The residue was triturated with hot ethanol and filtered to give 3-(3-ethoxy-6-ethoxycarbonyl-5-hydroxy-1,8-naphthyridin-2-yl)acrylic acid, m.p.>280° C.

b) A solution of the acrylic acid from a) above (10 g) in t-butanol (2.2 l) was formed by boiling the mixture under reflux with stirring. Heating was discontinued and a solution of potassium carbonate (8.9 g) in water (250 ml) was added rapidly dropwise. A solution of sodium periodate (62 g) in water (600 ml), preheated to 60° C., was added in portions over 2 hours. A solution of potassium permanganate (0.72 g) in water (500 ml) was added dropwise until a purple colour was obtained. The resultant mixture was stirred at ambient temperature for 7 hours adding more permanganate as required to retain the purple colour. The mixture was boiled under reflux and the remaining permanganate solution added. The mixture was then stirred at ambient temperature for 16 hours. Solid sodium metabisulphite was added until the mixture was colourless. The t-butanol was removed under reduced pressure. The residue was diluted with water (500 ml) and acidified with concentrated hydrochloric acid. On extracting this mixture with dichloromethane, a solid precipitated and this was collected by filtration. This solid was added to dilute sodium bicarbonate solution and the insoluble impurities removed by filtration. The filtrate was acidified and on shaking with dichloromethane a solid precipitated. This solid was collected by filtration to give 3-ethoxy-6-ethoxycarbonyl-5-hydroxy-1,8-naphthyridine-2-carboxylic acid, m.p.270°–272° C.

c) The acid from b) above (1.0 g) was added in portions to boiling diphenyl ether (100 ml) with stirring under reflux.

The mixture was boiled for 10 minutes after the addition and then cooled to ambient temperature. Petroleum ether b.p. 60°–80° C. was added and the solid collected by filtration to give ethyl 6-ethoxy-4-hydroxy-1,8-naphthyridine-3-carboxylate dihydrate, m.p.262°–264° C.

Example A4 a) A mixture of ethyl butyrylacetate (105.1 g), acetic anhydride (126 ml) and triethylorthoformate (117 ml) was stirred and boiled under reflux for 1.5 hours. The low boiling materials were distilled off under reduced pressure and the residue distilled under high vacuum to give ethyl 2-(ethoxymethylene)-3-oxohexanoate, b.p. 109°– 120° C. (0.4 mmHg).

b) Ethyl 2-(ethoxymethylene)-3-oxohexanoate (22.4 g) was added to a suspension of 5-ethoxy-6-methylpyridin-2-amine (14.9 g) in IMS (50 ml). After the initial exotherm had subsided IMS (100 ml) was added and the mixture boiled under reflux until a solution was obtained. This solution was cooled and filtered to give ethyl 2-(5-ethoxy-6-methylpyrid-2-ylaminomethylene)-3-oxohexanoate, m.p. 117°–120° C.

c) The product from b) (28 g) was added in portions over 3 minutes with stirring to diphenyl ether (500 ml) at 250° C. The mixture was boiled under reflux for 2 hours, cooled, diluted with petroleum ether b.p. 40°–60° C. (400 ml) and filtered to give 1-(6-ethoxy-4-hydroxy-7-methyl-1,8-naphthyridin-3-yl)-1-butanone, m.p. 240°– 241° C.

Example A5 a) A mixture of 6-ethoxypyridin-2-amine (8.0 g) and diethyl ethoxymethylenemalonate (12.5 g) was heated at 95° C. under vacuum for 3 hours and then heated at 95° C. at atmospheric pressure for 18 hours. The mixture was cooled to ambient temperature, diluted with petroleum ether b.p. 40°–60° C. and filtered to give diethyl (6-ethoxy-2-pyridylamino)methylenemalonate, m.p. 58°–60° C.

b) The malonate from a) (15.3 g) was dissolved in diphenyl ether (50 ml) and added dropwise to boiling diphenyl ether (75 ml). The mixture was boiled under reflux for 45 minutes, then cooled and diluted with petroleum ether b.p. 60°–80° C. The mixture was filtered to give ethyl 7-ethoxy-4-hydroxy-1,8-naphthyridine-3-carboxylate, m.p. 175°–179° C.

Example A6

Ethyl 6-bromo-4-hydroxy-7-methyl-1,8-naphthyridine-3-carboxylate was prepared from 6-amino-3-bromo-2-methylpyridine (prepared by the bromination of 6-amino-2-methylpyridine) as described in UK 1,000,982.

Example A7

A mixture of ethyl 6-bromo-4-hydroxy-7-methyl-1,8-naphthyridine-3-carboxylate (6.7 g), sodium hydroxide pellets (1.7 g) and water (50 ml) was heated at 180° C. in a pressure vessel for 18 hours. The mixture was cooled and filtered to give 6-bromo-7-methyl-1,8-naphthyridin-4-ol, m.p. >250° C.

Example A8

This example was carried out in a similar manner to Example A1.

a) 3-Hydroxy-2-methylpyridine (50 g) was added to a solution of sodium (11.6 g) in propan-1-ol (250 ml) and the mixture treated with 1-bromopropane (51 ml) in propan-1-ol (50 ml) to give 2-methyl-3-propoxypyridine, b.p. 96°–104° C. (30 mmHg).

b) The propoxypyridine (30.0 g) was dissolved in concentrated sulphuric acid (100 ml) and treated with a mixture of concentrated nitric acid (17 ml) and concentrated sulphuric acid (20 ml) at 0°–5° C. to give 2-methyl-6-nitro-3-propoxypyridine, m.p. 54°–56° C.

c) The nitropyridine (36.1 g), reduced iron powder (42.0 g), IMS (670 ml) and water (140 ml) were boiled and stirred under reflux while hydrochloric acid (15.3 ml) was added dropwise, to give 6-methyl-5-propoxypyridin-2-amine, as an oil.

d) The product from (c) (17.9 g), diethyl ethoxymethylenemalonate (22 ml) and IMS (50 ml) were boiled under reflux for 2 hours to give diethyl 2-(6-methyl-5-propoxy-2-pyridylaminomethylene)malonate, m.p. 116°–118° C.

e) The product from (d) (5 g) was added to diphenyl ether (100 ml) at 250° C. with stirring and the mixture boiled for 1 hour under reflux to give ethyl 4-hydroxy-7-methyl-6-propoxy-1,8-naphthyridine-3-carboxylate, m.p. 231°–5° C. (with decomposition).

Example A9

This example was carried out in a similar manner to A1.

a) A mixture of sodium methoxide (prepared from sodium metal) (10.2 g) and methanol (175 ml), 3-hydroxy-2-methylpyridine (43.0 g) phenyltrimethylammonium chloride (81.9 g) and DMF (400 ml) was boiled under reflux with stirring for 5 hours under nitrogen. The mixture was filtered and distilled. The fraction boiling at 167°– 195° C. was collected and purified by flash chromatography on silica using dichloromethane and then IMS as the mobile phase to give 3-methoxy-2-methylpyridine which was used without further purification.

b) The methoxypyridine (24.2 g) was dissolved in concentrated sulphuric acid (100 ml) and treated with a mixture of concentrated nitric acid (16.5 ml) and concentrated sulphuric acid (20.0 ml) which was added dropwise with stirring at 5° C., to give 3-methoxy-2-methyl-6-nitropyridine, m.p. 96°–98° C.

c) The nitropyridine (18.0 g), reduced iron powder (24.4 g), IMS (390 ml) and water (82 ml) were boiled and stirred under reflux while concentrated hydrochloric acid (9.0 ml) was added cautiously, dropwise, to give 5-methoxy-6-methylpyridin-2-amine, m.p. 98°–100° C.

d) A mixture of this pyridinamine (3.0 g), diethyl ethoxymethylenemalonate (4.4 ml) and IMS (10 ml) was boiled under reflux for 2 hours to give diethyl 2-(5-methoxy-6-methyl-2-pyridylaminomethylene)malonate, m.p. 109°–110° C.

e) The malonate (6.2 g) was added to boiling diphenyl ether (140 ml) with stirring, and the mixture stirred at reflux for 45 minutes, to give ethyl 4-hydroxy-6-ethoxy-7-methyl-1,8-naphthyridine-3-carboxylate, m.p. 262°– 265° C.

Example A10

A mixture of 6-ethoxy-7-methyl-1,8-naphthyridin-4-ol, (5.0 g) in glacial acetic acid (60 ml) was stirred at between 15°–20° C. while a solution of bromine (2.4 ml) in glacial acetic acid (10 ml) was added dropwise over 10 minutes. The mixture was stirred at ambient temperature for 1.5 hours and then filtered. The residue was washed with water, ground up in water and the mixture basified with sodium bicarbonate and filtered. The solid obtained was ground in sodium bisulphite solution and filtered to give 3-bromo-6-ethoxy-7-methyl-1,8-naphthyridin-4-ol, m.p. 266°–267° C.

Example A11

A mixture of 5-ethoxy-6-methyl-pyridin-2-amine (22.0 g) and ethyl acetoacetate (22.4 ml) was stirred at ambient temperature while polyphosphoric acid (47 ml) was added slowly. After the addition the mixture was warmed gradually on a steam bath, with caution, until an exotherm occurred with considerable frothing. After the reaction had subsided the mixture was heated for 75 minutes at 95° C., then cooled and added to ice/water. When all the polyphosphoric acid had dissolved the mixture was basified with 5M sodium hydroxide solution and the mixture extracted with dichloromethane to give 7-ethoxy-2,6-dimethylpyrido[1,2-a]pyrimidin-4-one m.p. 112°–114° C. The pyrimidine (12.3 g) was added to stirred paraffin oil (190 ml) at 340° C. over 10 minutes. The mixture was heated at 340° C. for a further 40 minutes then cooled to ambient temperature and diluted with petroleum ether, b.p. 60°–80° C. (180 ml). The mixture was filtered and the solid obtained was washed with ether. The solid was recrystallised from IMS to give 6-ethoxy-2,7-dimethyl-1,8-naphthyridin-4-ol, m.p. 281°–4° C.

Example A12 a) A mixture of ethyl formate (55.2 g) and ethyl propionate (51.0 g) was added dropwise with stirring to a suspension of sodium hydride (20.9 g, 60% dispersion in mineral oil) in dry THF (260 ml) under nitrogen. On completion of the addition, the temperature of the reaction mixture rose gradually from ambient temperature to 45° C. accompanied by rapid evolution of hydrogen. The reaction mixture was stirred for 2 hours then cooled and water (400 ml) was added cautiously. The basic solution was washed with ether, then acidified with dilute hydrochloric acid and extracted with ether to give an oil. The oil was distilled and the fraction boiling in the range 100°–160° C. was collected to give ethyl 2-formylpropionate.

b) The product from part a) (19.0 g) was added dropwise to 5M sodium hydroxide solution (29 ml) and water (100 ml) keeping the temperature below 15° C. This solution was then added quickly to the solution of 5-ethoxy-6-methyl-pyridin-2-amine (20.0 g) in 4M hydrochloric acid (40 ml) and water (200 ml). This mixture was stirred at ambient temperature for 2 hours then filtered to give a solid which was recrystallised from IMS/water to give ethyl 2-(5-ethoxy-6-methylpyridin-2-ylaminomethylene)propionate, m.p. 118°–122° C.

c) The product from part b) (11.9 g) was added to paraffin oil (500 ml) at 320° C. with stirring. Heating was continued at this temperature for 50 minutes and the reaction mixture allowed to cool. The mixture was poured into petroleum ether b.p. 40°–60° C. (1l) and the mixture filtered to give 6-ethoxy-3,7-dimethyl-1,8-naphthyridin-4-ol, m.p. 238°–242° C.

Example A13

A mixture of ethyl 6-ethoxy-4-hydroxy-7-methyl-1,8-naphthyridine-3-carboxylate (10.0 g), 5M sodium hydroxide solution (200 ml), IMS (64 ml) and water (64 ml) was boiled under reflux for 2 hours. The mixture was cooled to ambient temperature and then filtered. The residue was dissolved in water, acidified to pH 5 with glacial acetic acid and filtered. The residue was triturated with hot IMS, cooled and filtered to give 6-ethoxy-4-hydroxy-7-methyl-1,8-naphthyridine-3-carboxylic acid, m.p. 259°–261° C.

Example B1

Ethyl 6-ethoxy-4-hydroxy-7-methyl-1,8-naphthyridine-3-carboxylate (2.5 g) was added to phosphorus oxychloride (20 ml) with stirring at ambient temperature. The mixture was warmed to 40° C. and kept at this temperature for 1 hour then cooled to 10° C. The mixture was added to excess ice/water and the mixture basified with aqueous ammonia solution (specific gravity 0.88) while keeping the temperature below 5° C. The product was extracted into dichloromethane. The combined dichloromethane extracts were evaporated under reduced pressure at ambient temperature to give ethyl 4-chloro-6-ethoxy-7-methyl-1,8-naphthyridine-3-carboxylate, m.p. >250° C.

Example B2–B12

In a similar manner to that described in Example B1, a compound of formula V was treated with phosphorus oxychloride ($POCl_3$) to produce a compound of formula III in which $R_{15}$ represents chloro. The substituents $R_1$, $R_2$, $R_3$ and $R_4$ on compounds of formula V and III and the reaction conditions are shown in Table 1. $R_5$ is hydrogen in each example.

TABLE 1

| | Substituents | | | | Amt of Reactants | | Reaction Temp (°C.) | Reaction Time (minutes) |
|---|---|---|---|---|---|---|---|---|
| Ex | R1 | R2 | R3 | R4 | Starting Compound IV (g) | $POCl_3$ (ml) | | |
| B2 | $CH_3$ | $OC_2H_5$ | H | H | 2.5 | 25 | 60 | 60 |
| B3 | $CF_3$ | H | H | $COOC_2H_5$ | 3.4 | 30 | 90 | 75 |
| B4 | H | $OC_2H_5$ | H | $COOC_2H_5$ | 2.0 | 40 | 50 | 120 |
| B5 | $CH_3$ | $OC_2H_5$ | H | $COC_3H_7$ | 6.0 | 50 | 40–50 | 60 |
| B6 | $OC_2H_5$ | H | H | $COOC_2H_5$ | 8.8 | 50 | 80 | 25 |
| B7 | $CH_3$ | Br | H | $COOC_2H_5$ | 3.5 | 20 | 30 | 60 |
| B8 | $CO_2CH_3$ | H | H | H | 35.9 | 150 | 60 | 120 |
| B9 | $CH_3$ | $OC_3H_7$ | H | $COOC_2H_5$ | 1.8 | 15 | 40 | 60 |
| B10 | $CH_3$ | $OCH_3$ | H | $COOC_2H_5$ | 2.5 | 20 | 40 | 60 |
| B11 | $CH_3$ | $OC_2H_5$ | H | Br | 3.0 | 40 | 90 | 30 |
| B12 | $CH_3$ | $OC_2H_5$ | H | $CH_3$ | 3.5 | 30 | 95 | 90 |

Ex = Example
Amt = Amount
Temp = Temperature

The compounds prepared in Examples B2–B12 were as follows:

B2: 5-Chloro-3-ethoxy-2-methyl-1,8-naphthyridine, m.p. 164° C.

B3: Ethyl 4-chloro-7-trifluoromethyl-1,8-naphthyridine-3-carboxylate, m.p. 250°–252° C.

B4: Ethyl 4-chloro-6-ethoxy-1,8-naphthyridine-3-carboxylate, m.p. 243°–250° C.

B5: 1-(4-Chloro-6-ethoxy-7-methyl-1,8-naphthyridine-1-yl)-1-butanone, m.p. 137°–139° C.

B6: Ethyl 4-chloro-7-methyl-1,8-naphthyridine-3-carboxylate, m.p. 72°–75° C.

B7: Ethyl 6-bromo-4-chloro-7-methyl-1,8-naphthyridine-3-carboxylate, m.p. 222°–224° C.

B8: Methyl 5-chloro-1,8-naphthyridine-2-carboxylate, m.p. 128°–133° C.

B9: Ethyl 4-chloro-7-methyl-6-propoxy-1,8-naphthyridine-3-carboxylate, m.p. 100°–106° C.

B10: Ethyl 4-chloro-6-methoxy-7-methyl 1-1,8-naphthyridine-3-carboxylate, m.p. 130° C.

B11: 6-Bromo-5-chloro-3-ethoxy-2-methyl-1,8-naphthyridine, m.p. 194°–195° C.

B12: 5-Chloro-2,6-dimethyl-3-ethoxy-1,8-naphthyridine, m.p. 140°–144° C.

Example B13

In a similar manner to Example B1, a mixture of 6-bromo-7-methyl-1,8-naphthyridin-4-ol (3.7 g) and phosphorus oxychloride (25 ml) was stirred at 95° C. for 1 hour to give 3-bromo-5-chloro-2-methyl-1,8-naphthyridine, m.p. 160°–164° C.

Example B14

6-Ethoxy-4-hydroxy-7-methyl-1,8-naphthyridine-3-carboxylic acid (8.7 g) was added with stirring to phosphorus oxychloride (75 ml) at ambient temperature. The mixture was heated at 60° C. (internal temperature) for 45 minutes and then cooled to 10° C. The mixture was added dropwise to aqueous ammonia solution (specific gravity 0.88) at 10° C. over 4 hours. The mixture was filtered and the solid obtained was washed with absolute ethanol (7×100 ml). The combined washings were evaporated under reduced pressure to give 4-chloro-6-ethoxy-7-methyl-1,8-naphthyridine-3-carboxamide, which was used without further purification.

Example B15

6-Ethoxy-2,7-dimethyl-1,8-naphthyridin-4-ol (2.77 g) was added to phosphorus oxychloride (25 ml) at ambient temperature. The mixture was then heated at 95° C. for 1 hour. The mixture was worked up as described in example B1 to give 5-chloro-3-ethoxy-2,7-dimethyl-1,8-naphthyridine, m.p. 144°–7° C.

Example C1

N,N-Diethyl-2-(4-nitrophenoxy)ethylamine (4.0 g) (prepared by the method described in Helv. Chim. Acta. 1960, 43, 1971) was dissolved in IMS (70 ml), water (10 ml) and concentrated hydrochloric acid (2 ml). The mixture was boiled under reflux and then reduced iron powder (4.6 g) was carefully added in portions. The mixture was boiled under reflux for 7 hours then hot filtered. The filtrate was basified with 5M sodium hydroxide solution and then evaporated under reduced pressure. The residue was partitioned between water and ether. The organic layer was separated, dried and evaporated to give 4-[2-(N,N-diethylamino)ethoxy]aniline as an oil.

Example C2

4-(1-Adamantyloxy)aniline was prepared as described in J. Med. Chem. 1979, 22, 69.

Example C3

A solution of 3-(4-nitrophenoxy)propane-1,2-diol (5.0 g) in absolute ethanol (250 ml) was hydrogenated at atmospheric pressure in the presence of 10% palladium on charcoal (150 mg). After the uptake of hydrogen had ceased, the catalyst was removed by filtration. The filtrate was evaporated under reduced pressure to give 3-(4-aminophenoxy)propane-1,2-diol as a solid which was used without further purification.

Example C4

2-(4-Aminophenoxy)ethanol was prepared, using the method described in Example C3, by the reduction of 2-(4-nitrophenoxy)ethanol which was prepared by heating a mixture of 4-chloronitrobenzene, ethylene glycol and sodium carbonate in a sealed vessel (Beil. 6, II, 222).

Example C5

4-Amino-2,6-dimethylphenol hydrochloride was prepared by reduction of 2,6-dimethyl-4-nitrophenol using the method described in Example C1. The free base initially obtained was dissolved in dichloromethane and concentrated hydrochloric acid was added to this solution to obtain the product.

Preparation of Compounds of Formula I

EXAMPLE 1

A mixture of ethyl 4-chloro-6-ethoxy-7-methyl-1,8-naphthyridine-3-carboxylate (3.5 g) and 4-methoxyaniline (1.5 g) in ethanol (50 ml) was boiled under reflux for 1.5 hours. The reaction mixture was concentrated to half the volume, cooled and ether added. The solid was collected by filtration and dried to give ethyl 4-(4-methoxyanilino)-6-ethoxy-7-methyl-1,8-naphthyridine-3-carboxylate hydrochloride m.p. 260°–262° C. (with decomposition).

Active (1/2) 10 mg/kg; Active (4/5) 30 mg/kg.

EXAMPLE 2–33

In a similar manner to Example 1, compounds of formula I were prepared by reacting a compound of formula III with a compound of formula IV, in which $OR_6$ is located in the 4-position, as summarised in Table 2.

TABLE 2

| Ex | III | Weight of III (g) | Substituents on IV R_7 | R_8 | R_6 | Weight of IV (g) | EtOH (ml) | Reflux Time (Hours) | Notes |
|---|---|---|---|---|---|---|---|---|---|
| 2 | B2 | 2.0 | H | H | $CH_3$ | 0.84 | 25 | 5 | 1 |
| 3 | B3 | 2.7 | H | H | $CH_3$ | 1.1 | 50 | 2 | 2 |
| 4 | B4 | 1.8 | H | H | $CH_3$ | 0.79 | 50 | 1 | 2 |
| 5 | B5 | 3.3 | H | H | $CH_3$ | 1.4 | 95 | 18 | 3 |
| 6 | B6 | 6.9 | H | H | $CH_3$ | 3.0 | 100 | 17 | 4 |
| 7 | B7 | 1.7 | H | H | $CH_3$ | 0.64 | 25 | 1.5 | 2 |
| 8 | B13 | 1.5 | H | H | $CH_3$ | 0.80 | 25 | 24 | 5 |
| 9 | B1 | 2.0 | H | H | $(CH_2)_2OH$ | 0.92 | 45 | 18 | 6 |
| 10 | B1 | 2.0 | 2-$CH_3$ | H | $CH_3$ | 0.93 | 40 | 6.5 | 7 |
| 11 | B2 | 2.0 | 2-$CH_3$ | H | $CH_3$ | 1.2 | 35 | 6.75 | 7 |
| 12 | B2 | 2.0 | H | H | $CH_2CH_2N(C_2H_5)_2$ | 1.8 | 55 | 18 | 8 |
| 13 | B2 | 1.9 | 3-$CH_3$ | 5-$CH_3$ | H | 1.6 | 30 | 3 | 5 |
| 14 | B2 | 2.0 | H | H | 1-Adamantyl | 2.2 | 45 | 18 | 3 |
| 15 | B2 | 2.0 | H | H | Ph | 1.75 | 40 | 20 | 5 |
| 16 | B1 | 2.0 | H | H | $C_2H_5$ | 0.93 | 45 | 18 | 3 |
| 17 | B1 | 2.0 | H | H | $CF_3$ | 1.3 | 45 | 18 | 3 |
| 18 | B1 | 2.0 | H | H | $CH_2Ph$ | 1.35 | 45 | 18 | 3 |
| 19 | B8 | 14.0 | H | H | $CH_3$ | 7.74 | 200 | 18 | |
| 20 | B1 | 2.2 | H | H | $CH_2CH(OH)CH_2OH$ | 1.36 | 50 | 18 | 3 |
| 21 | B1 | 0.78 | 3-$CH_3$ | H | H | 0.33 | 35 | 5 | 3 |
| 22 | B1 | 2.0 | H | H | $(CH_2)_2N(C_2H_5)_2$ | 1.30 | 50 | 18 | 3 |
| 23 | B1 | 2.9 | 3-$CH_3$ | 5-$CH_3$ | $CH_3$ | 1.36 | 40 | 2 | 9 |
| 24 | B2 | 2.0 | 3-Cl | 5-Cl | H | 1.60 | 50 | 18 | 3 |
| 25 | B14 | 6.7 | H | H | $CH_3$ | 3.10 | 110 | 2 | 9 |
| 26 | B9 | 1.7 | H | H | $CH_3$ | 0.70 | 140 | 2 | 4 |
| 27 | B10 | 2.34 | H | H | $CH_3$ | 1.10 | 40 | 2 | 4 |
| 28 | B11 | 2.8 | H | H | $CH_3$ | 1.14 | 125 | 3.3 | 5 |
| 29 | B1 | 3.0 | H | 3-$CO_2H$ | H | 1.64 | 100 | 2.5 | 5 |
| 30 | B15 | 1.97 | H | H | $CH_3$ | 1.10 | 140 | 2.5 | 2 |
| 31 | B12 | 3.45 | H | H | $CH_3$ | 1.80 | 30 | 18 | 5 |
| 32 | B1 | 2.0 | 3-$OCH_3$ | 5-$OCH_3$ | $CH_3$ | 1.25 | 35 | 4.5 | 7 |
| 33 | B2 | 1.08 | H | H | $CH_2CH(OH)CH_2OH$ | 0.90 | 30 | 18 | 3 |

Notes to Table 2
(1) No ether added after concentration of the reaction mixture.
(2) Reaction mixture not concentrated but diluted with ethyl acetate to induce crystallisation.
(3) Reaction mixture not concentrated but diluted with ether to induce crystallisation.
(4) The reaction mixture was cooled and basified with triethylamine. This mixture was partitioned between water and ethyl acetate. The organic layer was separated and purified by flash chromatography on silica using ethyl acetate as the mobile phase. The main fractions were combined and evaporated. This residue was dissolved in IMS and hydrogen chloride gas passed through the solution. The solution was evaporated to dryness under reduced pressure. The residue was triturated with ether then filtered to give the product.
(5) The hydrochloride of the compound of formula IV was used. The reaction mixture was cooled and filtered to give the product.
(6) Ether was added to the cooled reaction mixture whereupon an oil separated out. The supernatant solvent was decanted from the oil and triturated with more ether to give a solid product which was collected by filtration.
(7) The reaction mixture was evaporated to dryness under reduced pressure and the residue triturated with ether to give a solid. The solid was collected by filtration, dissolved in IMS and purified by column chromatography using activated magnesium silicate as the stationary phase and IMS as the mobile phase.
(8) A few drops of concentrated hydrochloric acid were added to the initial reaction mixture. After heating, the mixture was cooled and filtered. The residue was recrystallised from IMS/ether.
(9) As in note 7 but dichloromethane was used as the mobile phase.

The compounds obtained in Examples 2–33 were as follows:

Example 2: 3-Ethoxy-5-(4-methoxyanilino)-2-methyl-1,8-naphthyridine hydrochloride, m.p. 246°–251° C. Active (2/2) at 30 mg/kg.

Example 3: Ethyl 4-(4-methoxyanilino)-7-trifluoromethyl-1,8-naphthyridine-3-carboxylate hemihydrochloride, m.p. 214°–217° C. Active (1/1) at 30 mg/kg.

Example 4: Ethyl 6-ethoxy-4-(4-methoxyanilino)-1,8-naphthyridine-3-carboxylate hydrochloride, m.p. 213°–215° C. Active (1/1) at 30 mg/kg.

Example 5: 3-Butyryl-6-ethoxy-4-(4-methoxyanilino)-7-methyl-1,8-naphthyridine hydrochloride, m.p. 236°–240° C. Borderline active (1/1) at 30 mg/kg.

Example 6: Ethyl 7-ethoxy-4-(4-methoxyanilino)-1,8-naphthyridine-3-carboxylate hydrochloride, m.p. 156°–160° C. Active (3/3) at 30 mg/kg.

Example 7: Ethyl 6-bromo-4-(4-methoxyanilino)-7-methyl-1,8-naphthyridine-3-carboxylate hydrochloride, m.p. 182°–185° C. (with decompositon). Active (1/2) at 30 mg/kg. Borderline active (1/2) at 30 mg/kg.

Example 8: 3-Bromo-5-(4-methoxyanilino)-2-methyl-1,8-naphthyridine, m.p. 164°–167° C. Borderline active (1/1) at 30 mg/kg.

Example 9: Ethyl 6-ethoxy-4-[4-(2-hydroxyethoxy)anilino]-7-methyl-1,8-naphthyridine-3-carboxylate hydrochloride, m.p. 190°–193° C. Active (2/2) at 30 mg/kg.

Example 10: Ethyl 6-ethoxy-4-(4-methoxy-2-methylanilino)-7-methyl-1,8-naphthyridine-3-carboxylate hemihydrochloride, m.p. 145°–147° C. Active (1/1) at 30 mg/kg.

Example 11: 3-Ethoxy-5-(4-methoxy-2-methylanilino)-2-methyl-1,8-naphthyridine sesquihydrochloride, m.p. 130° C. (with decomposition). Active (1/1) at 30 mg/kg.

Example 12: 4-[4-(2-Diethylaminoethoxy)anilino]-6-ethoxy-7-methyl-1,8-naphthyridine sesquihydrochloride hydrate, m.p. 154°–158° C. Borderline active (1/1) at 30 mg/kg.

Example 13: 4-(6-Ethoxy-7-methyl-1,8-naphthyridin-4-ylamino)-2,6-xylenol hydrochloride, m.p. 306°–308° C. (with decomposition). Active (2/2) at 30 mg/kg.
Example 14: 5-[4-(1-Adamantyloxy)anilino]-3-ethoxy-2-methyl-1,8-naphthyridine hydrochloride, m.p. 248°–252° C. Active (1/2) at 30 mg/kg.
Example 15: 3-Ethoxy-2-methyl-5-(4-phenoxyanilino)-1,8-naphthyridine hydrochloride, m.p. 268°–270° C. (with decomposition). A (1/2) 10 mg/kg, I (2/3) 30 mg/kg.
Example 16: Ethyl 6-ethoxy-4-(4-ethoxyanilino)-7-methyl-1,8-naphthyridine-3-carboxylate hydrochloride, m.p. 213°–215° C.
Example 17: Ethyl 6-ethoxy-7-methyl-4-(4-trifluoromethoxyanilino)-1,8-naphthyridine-3-carboxylate hydrochloride, m.p. 245°–250° C.
Example 18: Ethyl 4-(4-benzyloxyanilino)-6-ethoxy-7-methyl-1,8-naphthyridine-3-carboxylate hydrochloride, m.p. 213°–215° C.
Example 19: Methyl 5-(4-methoxyanilino)-1,8-naphthyridine-2-carboxylate, m.p. 228°–229° C.
Example 20: Ethyl 4-[4-(2,3-dihydroxypropoxy)anilino]-6-ethoxy-7-methyl-1,8-naphthyridine-3-carboxylate hydrochloride, m.p 192°–196° C. Borderline active (1/1) at 30 mg/kg.
Example 21: Ethyl 6-ethoxy-4-(4-hydroxy-3-methylanilino)-7-methyl1,8-naphthyridine-3-carboxylate hydrochloride, m.p. 210°–215° C.
Example 22: Ethyl 4-[4-(2-diethylaminoethoxy) anilino]-6-ethoxy-7-methyl-1,8-naphthyridine-3-carboxylate sesquihydrochloride, m.p. 135°–140° C. Active (1/1) at 30 mg/kg.
Example 23: Ethyl 6-ethoxy-4-(4-methoxy-3,5-dimethylanilino)-7-methyl-1,8-naphthyridine-3-carboxylate, m.p. 166°–168° C. Active (1/1) at 30 mg/kg.
Example 24: 2,6-Dichloro-4-(6-ethoxy-7-methyl-1,8-naphthyridin-4-ylamino)phenol sesquihydrochloride dihydrate, m.p. 181°–184° C.
Example 25: 6-Ethoxy-4-(4-methoxyanilino)-7-methyl-1,8-naphthyridine-3-carboxamide, m.p. 243°–245° C.
Example 26: Ethyl 4-(4-methoxyanilino)-7-methyl-6-propoxy-1,8-naphthyridine-3-carboxylate hydrochloride, m.p. 263°–266° C.
Example 27: Ethyl 6-methoxy-4-(4-methoxyanilino)-7-methyl-1,8-naphthyridine-3-carboxylate hemihydrochloride hydrate, m.p. 155°–159° C.
Example 28: 6-Bromo-3-ethoxy-5-(4-methoxyanilino)-2-methyl-1,8-naphthyridine hemihydrochloride hemihydrate, m.p. 134°–137° C. (after recrystallisation from ethanol).
Example 29: 5-(6-Ethoxy-3-ethoxycarbonyl-7-methyl-1,8-naphthyridin-4-ylamino)salicylic acid hydrochloride hemihydrate, m.p. 242°–246° C.
Example 30: 3-Ethoxy-5-(4-methoxyanilino)-2,7-dimethyl-1,8-naphthyridine hydrochloride, m.p.254°–256° C.
Example 31: 3-Ethoxy-5-(4-methoxyanilino)-2,6-dimethyl-1,8-naphthyridine hemihydrochloride hemihydrate, m.p. 135°–140° C.
Example 32: Ethyl 6-ethoxy-7-methyl-4-(3,4,5-trimethoxyanilino)-1,8-naphthyridine-3-carboxylate hemihydrochloride hydrate, m.p. 162°–164° C. Borderline Active (1/1) at 30 mg/kg.
Example 33: 3-[4-(6-Ethoxy-7-methyl-1,8-naphthyridin-4-ylamino)phenoxy]propane-1,2-diol hydrochloride, m.p. 229°–233° C.

EXAMPLE 34

In a similar manner to Example 1, a mixture of 5-chloro-3-ethoxy-2-methyl-1,8-naphthyridine (2.0 g) and 2-methoxyaniline (1.05 g) in IMS (30 ml) was boiled under reflux for 6 hours then cooled and filtered to give 3-ethoxy-5-(2-methoxyanilino)-2-methyl-1,8 -naphthyridine hydrochloride, m.p. 250°–252° C. (with decomposition). Active (1/1) at 30 mg/kg.

EXAMPLE 35

In a similar manner to Example 1, a mixture of ethyl 4-chloro-6-ethoxy-7-methyl-1,8-naphthyridine-3 -carboxylate (1.93 g) and 4-phenoxyaniline (1.33 g) in IMS (40 ml) was boiled under reflux for 2 hours to give ethyl 6-ethoxy-7-methyl-4-(4-phenoxyanilino)-1,8 -naphthyridine-3-carboxylate hydrochloride, m.p. 213°–215° C. Active (1/2) at 30 mg/kg.

EXAMPLE 36

In a similar manner to Example 1, a mixture 5 -chloro-3-ethoxy-2-methyl-1,8-naphthyridine (2.3 g), 4 -aminophenol (1.13 g) and ethanol (25 ml) was boiled under reflux for 1 hour to give 4-(6-ethoxy-7-methyl)-1,8-naphthyridin-4-ylamino)phenol hydrochloride, m.p. 275°–280° C. Active (1/2) at 30 mg/kg.

EXAMPLE 37

In a similar manner to Example 1, a mixture of ethyl 4-chloro-6-ethoxy-7-methyl-1,8-naphthyridine-3 -carboxylate (2.43 g) and 4-methoxy-[-methylaniline (1.13 g) in IMS (25 ml) was boiled under reflux for 4 hours then concentrated and ether (10 ml) added at 0° C. A small amount of solid was removed by filtration. The filtrate was basified with triethylamine and the mixture separated by flash chromatography on silica using ethyl acetate as the mobile phase. The residue obtained was triturated with petroleum ether b.p. 40°–60° C. to give ethyl 6-ethoxy-4-(4-methoxy-[-methylanilino)-7-methyl-1,8-naphthyridine-3-carboxylate, m.p. 129°–132° C.

EXAMPLE 38

Lithium triethylborohydride (a 1M solution in THF, 47 ml) was added to a solution of ethyl 6-ethoxy-4-(4 -methoxyanilino)-7-methyl-1,8-naphthyridine-3-carboxylate (4.5 g) in THF (150 ml) with stirring under nitrogen at 0°–10° C. The mixture was allowed to warm up to ambient temperature and stirred at this temperature for 18 hours. Further lithium triethylborohydride solution (15 ml) was added and the solution stirred at ambient temperature for 4 hours. The reaction mixture was cooled to 5° C. and then 5M hydrochloric acid (5 ml) was added carefully followed by water (50 ml). The organic layer was separated and the aqueous layer extracted with ether. The aqueous layer was basified with 5M sodium hydroxide solution and extracted into ethyl acetate. The residue, obtained from the ethyl acetate extracts, was purified by flash chromatography on silica, using dichloromethane/IMS (15/1) as the mobile phase, to give 6-ethoxy-4-(4-methoxyanilino)-7-methyl-1,8-naphthyridin-3-ylmethanol, m.p. 193°–197° C.

EXAMPLE 39

A mixture of 3-ethoxy-5-(4-methoxyanilino)-2 -methyl-1,8-naphthyridine hydrochloride (5.0 g), glyoxylic acid monohydrate (2.2 g) and glacial acetic acid (50 ml) were stirred and treated dropwise with trifluoroacetic acid (12.5 ml). The mixture was stirred and heated at 95° C. for 22 hours and cooled to ambient temperature. The mixture was filtered and the solid obtained was stirred in sodium bicarbonate solution (100 ml) for 15 minutes. The mixture was filtered. The solid obtained was stirred in water (100 ml) and acidified with concentrated hydrochloric acid to pH 1. After stirring for an hour the mixture was filtered to give a solid. The filtrate was evaporated to dryness and the residue triturated with water and filtered. The crops of solid were combined, dissolved in dichloromethane/methanol, dried, filtered and evaporated. The residue was triturated with hot ethyl acetate and hot filtered. The solid obtained was combined with the solid obtained from the acidic mixture above, triturated with hot ethyl acetate and hot filtered. The solid obtained was purified by flash column chromatography on silica using a mixture of ethyl acetate:dichloromethane:methanol, 5:5:1 and then 1:1:1 to give a solid. The solid was triturated with hot ethyl acetate and hot filtered to give 3-[3-ethoxy-5-(4 -methoxyanilino)-1,8-naphthyridin-2-yl]acrylic acid hydrochloride dihydrate, m.p. 230°–235° C. (with decomposition).

EXAMPLE 40

A mixture of ethyl 6-ethoxy-4-(4-methoxyanilino)-7 -methyl-1,8-naphthyridine-3-carboxylate hydrochloride (4.76 g), glyoxylic acid (1.73 g) and glacial acetic acid (50 ml) was boiled under reflux for 24 hours. The mixture was cooled and a solid was collected by filtration. The filtrate was acidified with concentrated hydrochloric acid and filtered to give a second crop of solid. The two crops of solid were combined, stirred in water and the mixture basified with sodium bicarbonate. The pH of the mixture was adjusted to pH 6 with concentrated hydrochloric acid and the mixture was extracted with ethyl acetate and then with dichloromethane. The combined organic extracts were washed with water, dried and evaporated. The residue was triturated with ethyl acetate and then filtered to give 3-[3-ethoxy-6-ethoxycarbonyl-5-(4-methoxyanilino)-1,8-naphthyridin-2-yl]acrylic acid hemihydrochloride, m.p. 259°–261° C.

EXAMPLE 41

A mixture of 3-[3-ethoxy-6-ethoxycarbonyl-5-(4 -methoxyanilino)-1,8-naphthyridin-2-yl]acrylic acid (2.3 g), 10% palladium on charcoal (0.5 g), IMS (250 ml) and concentrated hydrochloric acid (0.4 ml) was shaken under an atmosphere of hydrogen until uptake of hydrogen ceased. The catalyst was removed by filtration and the filtrate was evaporated. The residue was triturated with hot ethyl acetate and hot filtered to give 3-[3 -ethoxy-6-ethoxycarbonyl-5-(4-methoxyanilino)-1,8 -naphthyridin-2-yl]propionic acid hydrochloride, m.p. 213°–216° C.

EXAMPLE 42

A mixture ethyl 6-ethoxy-4-(4-methoxyanilino)-7 -methyl-1,8-naphthyridine-3-carboxylate (6.38 g), water (40 ml), sodium hydroxide solution (120 ml, 0.6M) was boiled and stirred under reflux for 2 hours and then allowed to cool. The mixture was acidified with 5M hydrochloric acid (100 ml) and filtered. The filtrate was extracted with dichloromethane to give a residue which was washed with 5M hydrochloric acid and filtered to give 6-ethoxy-4-(4-(methoxyanilino)-7-methyl-1,8 -naphthyridine-3-carboxylic acid, m.p. 259°–263° C.

EXAMPLE 43

A mixture of ethyl 7-ethoxy-4-(4-methoxyanilino)-1,8-naphthyridine-3-carboxylate hydrochloride (2.6 g) and 5M sodium hydroxide solution (60 ml) was heated on a steam bath for 4 hours. The mixture was cooled and filtered. The residue was dissolved in IMS and hydrogen chloride gas bubbled through this solution. Ether was added to induce crystallisation and the mixture was filtered to give ethyl 4-[4-methoxyanilino]-7-oxo-7,8 -dihydro-1,8-naphthyridine-3-carboxylate 0.3 hydrochloride hemihydrate, m.p. 243°–246° C.

EXAMPLE 44

A mixture of methyl 5-(4-methoxyanilino)-1,8 -naphthyridine-2-carboxylate (1.0 g) and dry THF (100 ml) was stirred at 0° C. while lithium triethylborohydride (a 1M solution in THF, 6.5 ml) was added over 10 minutes. After stirring at 0° C. for 1 hour further lithium triethylborohydride solution (3 ml) was added. The mixture was stirred for a further 1.5 hours at 0° C. Water (100 ml) was added cautiously and the mixture was extracted with ethyl acetate. The ethyl acetate extract was extracted with 0.5M hydrochloric acid. The acid extract was washed with ethyl acetate, basified with sodium bicarbonate and extracted with dichloromethane:methanol (3:1) (2×200 ml) to give a residue which was triturated with methanol and filtered. The solid obtained was triturated with ethyl acetate and filtered to give 5-(4-methoxyanilino)-1,8-naphthyridin-2-ylmethanol, m.p. 275°–281° C.

EXAMPLE 45

A solution of 3-butyryl-6-ethoxy-4-(4 -methoxyanilino)-7-methyl-1,8-naphthyridine (8.0 g) in absolute ethanol (200 ml) was added dropwise at 0° C. over 1 hour to a solution of sodium borohydride (2.4 g) in absolute ethanol (200 ml). The mixture was allowed to warm up to ambient temperature and stirred at this temperature for 18 hours. Glacial acetic acid was added carefully to destroy excess borohydride and the resulting mixture was concentrated under reduced pressure. The residue was dissolved in water (200 ml) and extracted with dichloromethane to give a residue which was dissolved in IMS and saturated with hydrogen chloride gas. Ether was added to induce crystallisation. The mixture was filtered to give 1-[6 -ethoxy-4-(4-methoxyanilino)-7-methyl-1,8-naphthyridin-3 -yl]butan-1-ol, m.p. 120°–124° C.

EXAMPLE 46

A mixture of ethyl 4-(4-methoxyanilino)-6-ethoxy-7 -methyl-1,8-naphthyridine-3-carboxylate (2.9 g) in dichloromethane (45 ml) was added rapidly to a suspension of powdered anhydrous aluminium chloride (12.8 g) in dichloromethane (115 ml) with stirring. The mixture was stirred for 24 hours at ambient temperature and then poured into ice/water. The mixture was stirred for 30 minutes then filtered. The residue was basified and partitioned between dichloromethane and water. The aqueous layer was evaporated to dryness. The residue was dissolved in propan-2-ol (150 ml) and then purified by column chromatography to give 6-hydroxy-4-(4 -methoxyanilino)-7-methyl-1,8-naphthyridine-3-carboxylic acid hemihydrate, m.p. 267°–268° C. (with decomposition).

EXAMPLE 47

In the preparation of capsules, 10 parts by weight of active compound and 240 parts by weight of lactose are de-aggregated and blended. The mixture is filled into hard gelatin capsules, each capsule containing 10 mg active compound.

EXAMPLE 48

Tablets are prepared from the following ingredients.

|  | Parts by Weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with magnesium stearate and the rest of the starch. The mixture is then compressed in a tabletting machine to give tablets containing 10 mg of active compound.

EXAMPLE 49

Tablets are prepared by the method of the previous Example. The tablets are enteric coated in a conventional manner using a solution of 20% cellulose acetate phthalate and 3% diethyl phthalate in ethanol:dichloromethane (1:1)

EXAMPLE 50

In the preparation of suppositories, 100 parts by weight of active compound is incorporated in 1300 parts by weight of semi-synthetic glycerides as the suppository base and the mixture formed into suppositories each containing 100 mg of active ingredient.

EXAMPLE 51

In the preparation of capsules, 50 parts by weight of active compound, 300 parts by weight of lactose and 3 parts by weight of magnesium stearate are de-aggregated and blended. The mixture is filled into hard gelatin capsules, each capsule containing 50 mg of active ingredient.

EXAMPLE 52

The active compound is incorporated into the base by thorough homogenization until the drug is evenly distributed. The ointment is packed into 10 g amber jars with screw-capped lined lids.

| Active compound | 0.1 g |
| --- | --- |
| White soft paraffin to | 10 g |

We claim:
1. Compounds of the formula I

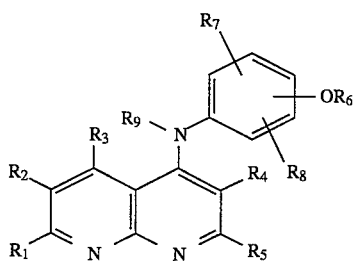

and pharmaceutically acceptable salts thereof, in which $R_1$ represents hydrogen, a $C_{1-6}$ alkyl group, hydroxy, a carboxy $C_{2-4}$ alkenyl group, a $C_{2-6}$ alkoxycarbonyl $C_{2-4}$ alkenyl group, a hydroxy $C_{1-6}$ alkoxycarbonyl $C_{1-4}$ alkyl group, a carboxy group, a $C_{2-6}$ alkoxycarbonyl group or a $C_{1-6}$ alkanoylamino group;

$R_2$ represents hydrogen, halo, a $C_{1-6}$ alkoxy group, hydroxy, a $C_{1-6}$ alkanoyloxy group, or a phenoxy group (which may be optionally substituted by a $C_{1-4}$ alkyl group, halo or a $C_{1-4}$ alkoxy group);

$R_3$ represents hydrogen or a $C_{1-4}$ alkyl group;

$R_4$ represents hydrogen, halo, a $C_{2-7}$ alkoxycarbonyl group, a benzyloxycarbonyl group (which may be optionally substituted by a $C_{1-4}$ alkyl group, halo or a $C_{1-4}$ alkoxy group), a $C_{1-6}$ alkanoyl group, a benzoyl group (which may be optionally substituted by a $C_{1-4}$ alkyl group, halo or a $C_{1-4}$ alkoxy group), carbamoyl, a $C_{1-6}$ alkyl group, a carboxy group, a $C_{1-6}$ hydroxyalkyl group or a $C_{1-6}$ alkylthio group;

$R_5$ represents hydrogen or a $C_{1-4}$ alkyl group;

$R_6$ represents hydrogen, a $C_{1-6}$ alkyl group, optionally substituted by one or more of the following: hydroxy, halo or an amino group of formula $-NR_{12}R_{13}$ (in which $R_{12}$ and $R_{13}$ independently represent hydrogen or a $C_{1-4}$ alkyl group or $R_{12}$ and $R_{13}$ together with the nitrogen atom to which they are attached represent a pyrrolidine ring, a morpholine ring or a piperidine ring) a $C_{3-12}$ alicyclic hydrocarbon group, a phenyl group (which may be optionally substituted by a $C_{1-4}$ alkyl group, halo or a $C_{1-4}$ alkoxy group), a $C_{3-6}$ cycloalkyl $C_{1-4}$ alkyl group or a benzyl group (which may be optionally substituted by a $C_{1-4}$ alkyl group, halo or a $C_{1-4}$ group);

$R_7$ represents hydrogen, halo, trifluoromethyl, triflorormethoxy, a $C_{1-6}$ alkyl group, a carboxy group, or a $C_{1-6}$ alkoxy group;

$R_8$ represents hydrogen, halo, trifluoromethyl, trifluoromethoxy, a $C_{1-6}$ alkyl group or a $C_{1-6}$ alkoxy group; and $R_9$ represents hydrogen or a $C_{1-4}$ alkyl group; with the proviso that one of $R_1$, $R_2$ and $R_3$ is other than hydrogen, methyl or halo.

2. Compounds according to claim 1 represented by formula II

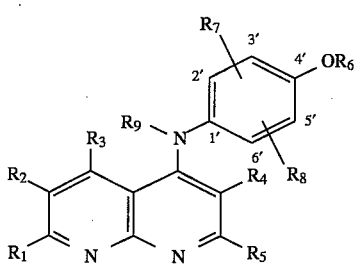

and pharmaceutically acceptable salts thereof in which $R_1$ represents hydrogen, a $C_{1-4}$ alkyl group, hydroxy, a carboxy $C_{2-4}$ alkenyl group, a $C_{2-6}$ alkoxycarbonylvinyl group, an ω-hydroxy $C_{1-4}$ alkyl group, a carboxy $C_{1-4}$ alkyl group, a $C_{2-6}$ alkoxycarbonyl $C_{1-4}$ alkyl group, a $C_{1-6}$ alkoxy group, or a polyhalogenated $C_{1-4}$ alkyl group;

$R_2$ represents hydrogen, halo, $C_{1-6}$ alkoxy group or hydroxy;

$R_3$ represents hydrogen;

$R_4$ represents hydrogen, halo, a $C_{2-5}$ alkoxycarbonyl group, benzyloxycarbonyl, a $C_{2-6}$ alkanoyl group carbamoyl, a $C_{1-4}$ alkyl group, carboxy or an α-hydroxy $C_{1-6}$ alkyl group;

$R_5$ represents hydrogen or a $C_{1-4}$ alkyl group;

$R_6$ represents hydrogen, a $C_{1-6}$ alkyl group, a $C_{3-12}$ alicyclic hydrocarbon group, phenyl or benzyl;

$R_7$ represents hydrogen, halo, trifluoromethyl, a $C_{1-4}$ alkyl group or a carboxy group;

$R_8$ represents hydrogen, halo, trifluoromethyl, a $C_{1-4}$ alkyl group or a $C_{1-4}$ alkoxy group; and $R_9$ represents hydrogen or a $C_{1-4}$ alkyl group.

3. Compounds according to claim 2 in which $R_1$ represents hydrogen, methyl, ethoxy, trifluoromethyl, hydroxy, 2-carboxyvinyl, 2-carboxyethyl or hydroxymethyl.

4. Compounds according to claim 2 in which $R_2$ represents hydrogen, methoxy, ethoxy, propoxy or bromo.

5. Compounds according to claim 2 in which $R_4$ represents hydrogen, bromo, ethoxycarbonyl, 1-butyryl, carboxy, carbamoyl, hydroxymethyl or 1-hydroxybutyl.

6. Compounds according to claim 2 in which $R_5$ represents hydrogen or methyl.

7. Compounds according to claim 2 in which $R_6$ represents hydrogen, methyl, ethyl, 1-adamantyl, phenyl, 2-(diethylamino)ethyl, 2-hydroxyethyl, 2,3-dihydroxypropyl, trifluoromethyl or benzyl.

8. Compounds according to claim 2 in which $R_7$ represents hydrogen, 2'-methyl, 3'-methyl, 3'-methoxy, 3'-chloro or 3'-carboxy.

9. Compounds according to claim 2 in which $R_8$ represents hydrogen, 5'-methyl, 5'-methoxy or 5'-chloro.

10. Compounds according to claim 2 in which $R_9$ represents hydrogen or methyl.

11. Compounds according to claim 2 in which $R_1$ represents hydrogen, a $C_{1-4}$ alkyl group or 2-carboxyvinyl; $R_2$ represents a $C_{2-4}$ alkoxy group; $R_3$ represents hydrogen; $R_4$ represents a $C_{3-4}$ alkoxycarbonyl group; $R_5$ represents hydrogen; $R_6$ represents a $C_{1-4}$ alkyl group, phenyl, benzyl, trifluoromethyl, 2-hydroxyethyl, 2-(diethylamino)ethyl, 2,3-dihydroxypropyl; $R_7$ represents hydrogen or 2'-methyl and $R_8$ and $R_9$ represent hydrogen.

12. Compounds according to claim 2 in which $R_1$ represents hydrogen, hydroxy, ethoxy or trifluoromethyl; $R_2$ represents hydrogen; $R_3$ represents hydrogen; $R_4$ represents a $C_{3-4}$ alkoxycarbonyl group; $R_5$ represents hydrogen; $R_6$ represents a $C_{1-4}$ alkyl group (which may be optionally substituted by one or more of the following: hydroxy, halo or an amino group of formula —$NR_{12}R_{13}$ in which $R_{12}$ and $R_{13}$ independently represents hydrogen or a $C_{1-4}$ alkyl group); and $R_7$, $R_8$ and $R_9$ each represent hydrogen.

13. Compounds according to claim 2 in which $R_1$ represents a $C_{1-4}$ alkyl group; $R_2$ represents a $C_{2-4}$ alkoxy group; $R_3$, $R_4$, $R_5$ and $R_6$ represent hydrogen; $R_7$ represents hydrogen or a $C_{1-4}$ alkyl group; $R_8$ represents hydrogen or a $C_{1-4}$ alkyl group; and $R_9$ represents hydrogen.

14. Compounds of formula I as claimed in claim 1 selected from:
Ethyl 6-ethoxy-4-(4-methoxyanilino)-7-methyl-1,8-naphthyridine-3-carboxylate,
3-Ethoxy-5-(4-methoxyanilino)-2-methyl-1,8-naphthyridine,
Ethyl 7-ethoxy-4-(4-methoxyanilino)-1,8-naphthyridine-3-carboxylate,
Ethyl 6-ethoxy-4-[4-(2-hydroxyethoxy)anilino]-7-methyl-1,8-naphthyridine-3-carboxylate and
4-(6-Ethoxy-7-methyl-1,8-naphthyridin-4-ylamino)-2,6-xylenol;
and pharmaceutically acceptable salts thereof.

15. A pharmaceutical composition containing a therapeutically effective amount of a compound of formula I as claimed claim 1 together with a pharmaceutically acceptable diluent or carrier.

16. A method of treating rheumatic diseases, comprising the administration of a therapeutically effective amount of a compound of formula I as claimed in claim 1 to a mammal in need thereof.

* * * * *

UNITED STATES PATENT AND TRADEMARK OFFICE
CERTIFICATE OF CORRECTION

PATENT NO. :   5,464,781
DATED      :   November 7, 1995
INVENTOR(S):   ARMITAGE et al.

It is certified that error appears in the above-identified patent and that said Letters Patent is hereby corrected as shown below:

Title page,

[22] line 1, change "Oct. 12, 1992" to read

-- Dec. 12, 1992 --.

Signed and Sealed this

Twenty-seventh Day of February, 1996

Attest:

BRUCE LEHMAN

Attesting Officer      Commissioner of Patents and Trademarks

UNITED STATES PATENT AND TRADEMARK OFFICE
CERTIFICATE OF CORRECTION

PATENT NO. : 5,464,781
DATED : November 7, 1995
INVENTOR(S) : Armitage, et. al.

It is certified that error appears in the above-indentified patent and that said Letters Patent is hereby corrected as shown below:

Title page, item [54] line 2, and col. 1, line 2, delete "ANTI-RHOUMATIC AGENTS" and insert therefor --ANTI -RHEUMATIC Agents--.

Column 5, line 65, after "acid" start new line with --6-Ethoxy-4-(4-methe--.

Column 30, line 46, after "or a piperidine ring)" insert --,--.

Signed and Sealed this

Fourth Day of June, 1996

Attest:

BRUCE LEHMAN

*Attesting Officer*  *Commissioner of Patents and Trademarks*